US012564529B2

(12) United States Patent
Boulos et al.

(10) Patent No.: US 12,564,529 B2
(45) Date of Patent: Mar. 3, 2026

(54) PATIENT TRANSFER DEVICE

(71) Applicant: Sage Products, LLC, Cary, IL (US)

(72) Inventors: Catherine Boulos, Vernon Hills, IL
(US); Brian Ecklund, McHenry, IL
(US); Kaitlin Konopacz, Cary, IL
(US); Heather Sirianni, Cary, IL (US)

(73) Assignee: Sage Products, LLC, Cary, IL (US)

( * ) Notice: Subject to any disclaimer, the term of this
patent is extended or adjusted under 35
U.S.C. 154(b) by 151 days.

(21) Appl. No.: 18/758,999

(22) Filed: Jun. 28, 2024

(65) Prior Publication Data

US 2024/0350345 A1 Oct. 24, 2024

Related U.S. Application Data

(62) Division of application No. 17/713,877, filed on Apr.
5, 2022, now Pat. No. 12,064,385.

(60) Provisional application No. 63/171,446, filed on Apr.
6, 2021.

(51) Int. Cl.
*A61G 7/10* (2006.01)
*A61F 13/15* (2006.01)
*A61F 13/505* (2006.01)

(52) U.S. Cl.
CPC .......... *A61G 7/1026* (2013.01); *A61F 13/505*
(2013.01); *A61G 7/1021* (2013.01); *A61F*
*2013/15154* (2013.01)

(58) Field of Classification Search
None
See application file for complete search history.

(56) References Cited

U.S. PATENT DOCUMENTS

| 3,769,642 | A | 11/1973 | Warman |
| 4,627,426 | A | 12/1986 | Wegener et al. |
| 7,114,204 | B2 | 10/2006 | Patrick |
| 7,650,654 | B2 | 1/2010 | Lambarth et al. |
| 7,735,164 | B1 | 6/2010 | Patrick |
| 7,861,335 | B2 | 1/2011 | Deluca et al. |
| 8,234,727 | B2 | 8/2012 | Schreiber et al. |
| 8,276,222 | B1 | 10/2012 | Patrick |
| 8,887,326 | B2 | 11/2014 | Patrick |
| 9,125,777 | B2 | 9/2015 | Patrick |
| 9,241,580 | B2 | 1/2016 | Patrick et al. |
| 9,314,388 | B2 | 4/2016 | Patrick |

(Continued)

FOREIGN PATENT DOCUMENTS

| GB | 2 387 540 | 10/2003 |
| WO | WO-2010/082021 | 7/2010 |

*Primary Examiner* — Adam C Ortiz
(74) *Attorney, Agent, or Firm* — Foley & Lardner LLP

(57) ABSTRACT

A patient transfer device includes a chamber formed by an
upper layer coupled to a lower layer, the chamber configured
to be inflated and supported by a support surface in contact
with the lower layer. The patient transfer device further
includes a port configured for connection to an air flow
device. In various embodiments, the patient transfer device
includes a low-friction sheet coupled to a bottom surface of
the lower layer, wherein the low-friction sheet is configured
to slide against itself to facilitate sliding of the chamber
relative to the support surface. In other embodiments, the
patient transfer device includes at least one air-expelling
region disposed within a bottom surface of the lower layer,
wherein the region is configured to expel air from within the
first chamber along the bottom surface of the lower layer to
facilitate sliding of the first chamber relative to the support
surface.

20 Claims, 34 Drawing Sheets

(56)　　　　　References Cited

U.S. PATENT DOCUMENTS

2013/0205495  A1　　8/2013　Ponsi et al.
2018/0353360  A1　　12/2018　Kea et al.

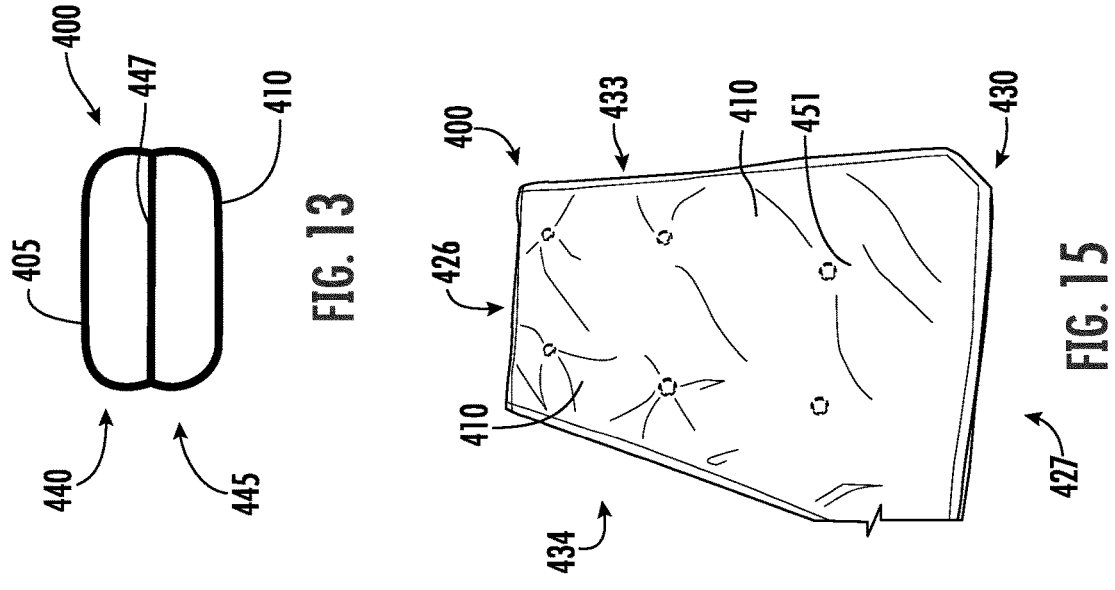
FIG. 13
FIG. 15
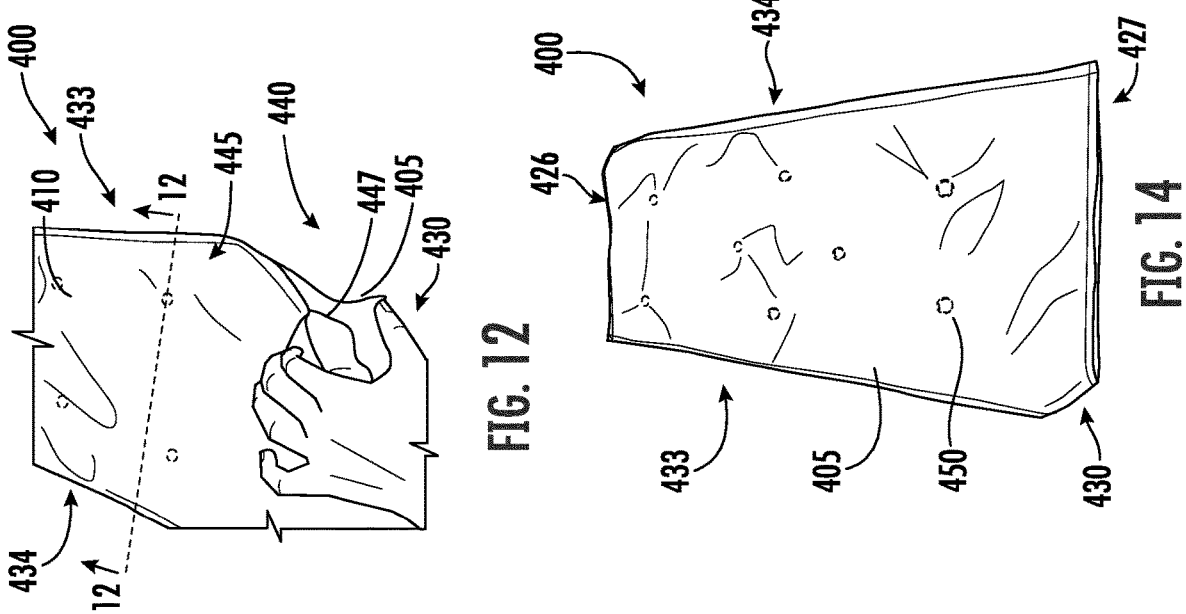
FIG. 12
FIG. 14

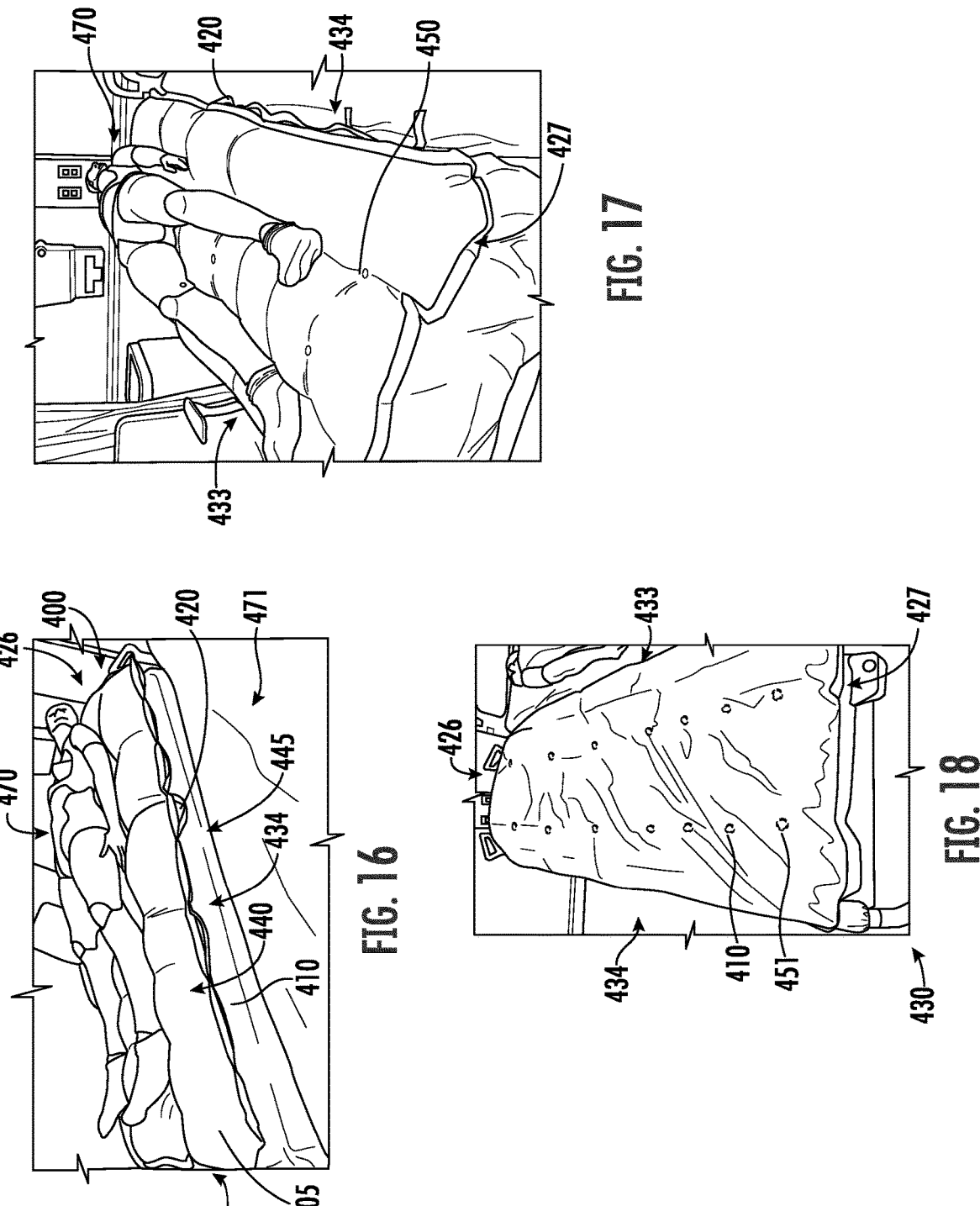

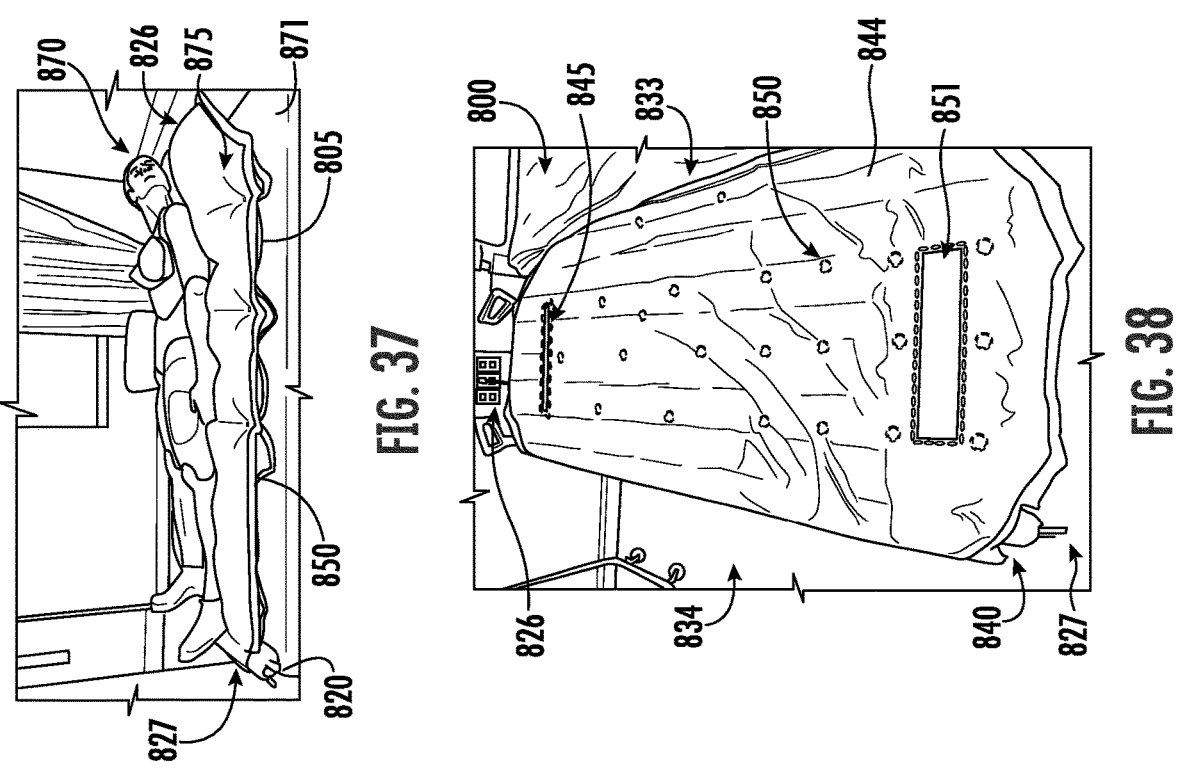
FIG. 37
FIG. 38
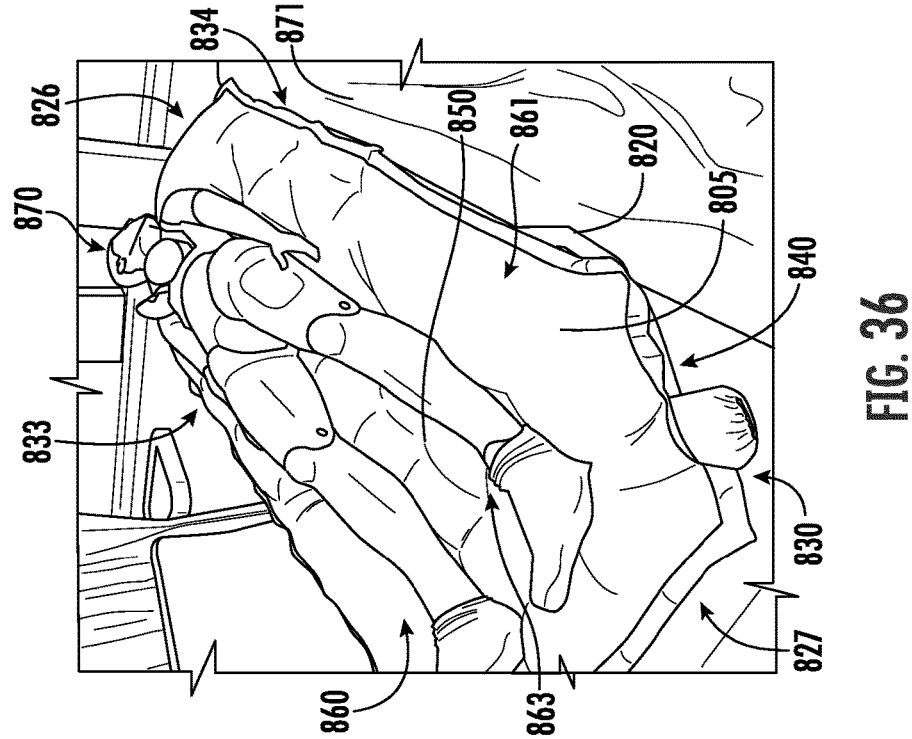
FIG. 36

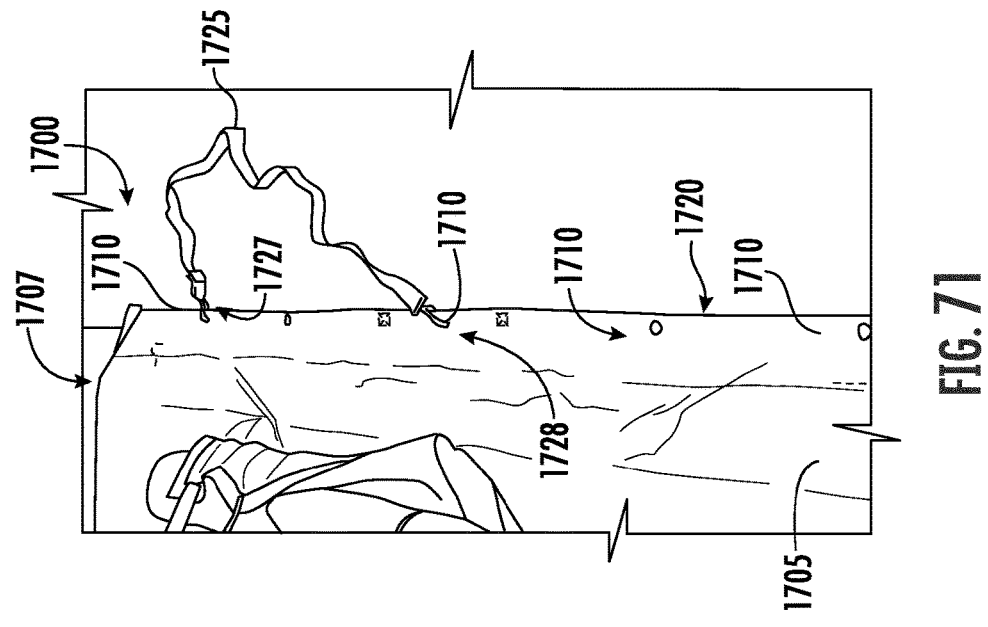
FIG. 71
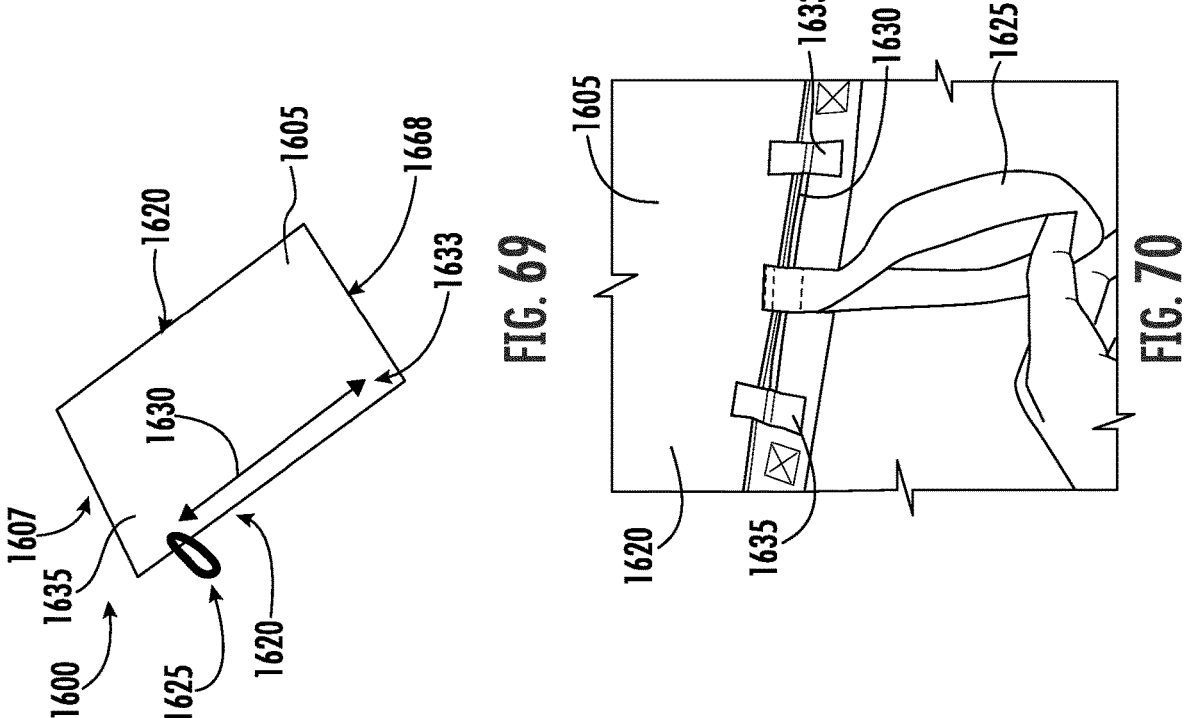
FIG. 69
FIG. 70

PATIENT TRANSFER DEVICE

CROSS-REFERENCE TO RELATED PATENT APPLICATIONS

This application is a Divisional of U.S. patent application Ser. No. 17/713,877, filed on Apr. 5, 2022, which claims the benefit of and priority to U.S. Provisional Patent Application No. 63/171,446, filed on Apr. 6, 2021, all of which are incorporated herein by reference in their entireties.

BACKGROUND

The present disclosure generally relates to the field of patient transfer in a clinical setting. More specifically, the present disclosure relates to patient transfer devices for facilitating patient transfer from one surface to another.

SUMMARY

According to one aspect of the present disclosure, a patient transfer device includes a chamber formed by an upper layer coupled to a lower layer, a port disposed along an outer perimeter of the chamber, the port configured for connection to an air flow device, and a low-friction sheet coupled to a bottom surface of the lower layer, the low friction sheet forming a loop. The low-friction sheet is coupled to the lower layer along a longitudinal line along a length of the lower layer. The chamber is configured to be inflated and supported by a support surface in contact with the lower layer. A first surface of the low-friction sheet is configured to engage the support surface and a second surface of the low-friction sheet is configured to slide against itself to facilitate sliding of the chamber relative to the support surface.

In various embodiments, the longitudinal line extends along a length of the lower layer. In other embodiments, the longitudinal line is disposed along a central portion of the lower layer. In some embodiments, the low-friction sheet is removable from the lower layer. In other embodiments, the low-friction sheet is selectively couplable to the lower layer such that the low-friction sheet may be coupled to the lower layer at a position based on a direction of intended sliding of the chamber. In various embodiments, the upper layer includes an absorbent pad. In some embodiments, the absorbent pad includes a plurality of layers and each layer is removable from the upper layer by separation along a central perforation.

According to another aspect of the present disclosure, a patient transfer device supported by a support surface includes an upper layer coupled to a lower layer at a top edge and a bottom edge, a low-friction intermediate layer disposed between the upper layer and the lower layer, and between the lower layer and the support surface, and at least one handle disposed along a first side edge of at least one of the upper layer or the lower layer, the first side edge disposed substantially perpendicular to the top edge and the bottom edge. The intermediate layer forms a loop about the lower layer such that the lower layer is disposed within the loop. The intermediate layer is further configured to slidably engage with the lower layer responsive to a pull force applied to the at least one handle. The slidable engagement of the intermediate layer facilitates sliding of the upper layer and lower layer relative to the support surface.

In various embodiments, the patient transfer devices includes one or more straps coupled to at least one of the first side edge or a second side edge, the second side edge opposite the first side edge, and the one or more straps being configured to reduce a pull force necessary to move the patient transfer device. In some embodiments, at least one of the upper layer, lower layer, or intermediate layer includes nylon.

According to yet another aspect of the present disclosure, a patient transfer device includes a first chamber formed by an upper layer coupled to a lower layer, a port disposed along an outer perimeter of the chamber, the port configured for connection to an air flow device, and at least one air-expelling region disposed within a bottom surface of the lower layer, the region configured to expel air from within the first chamber along the bottom surface of the lower layer. The chamber may be configured to be inflated and supported by a support surface, the support surface being in contact with the lower layer. Furthermore, the air expelled from within the first chamber may reduce an amount of contact between the support surface and the lower layer to facilitate sliding of the first chamber relative to the support surface.

In various embodiments, the patient transfer device includes a top layer coupled to the upper layer and the lower layer such that the upper layer and the top layer define a second chamber disposed above the first chamber formed by the upper layer and the lower layer. In some embodiments, the at least one air-expelling region disposed within the bottom surface of the lower layer includes a plurality of apertures and each of the plurality of apertures is configured expel air from within the first chamber. In various embodiments, at least one air-expelling region includes a porous material, wherein the porous material includes a plurality of pores through which air is expelled from the first chamber.

In some embodiments, the air-expelling region is disposed adjacent an outer perimeter of the first chamber such that the air-expelling region is configured to surround a non-porous region of the bottom surface of the lower layer. In various embodiments, the at least one air-expelling region is configured as a rectangular strip, the rectangular strip disposed near a top edge of the first chamber. In yet other embodiments, the bottom surface of the lower layer includes two air-expelling regions such that a first air-expelling region is disposed near a top edge of the first chamber and a second air-expelling region is disposed near a bottom edge of the first chamber. In various embodiments, at least one of a length or width of the second air-expelling region is less than at least one of a length or width of the first air-expelling region. In some embodiments, a width of the at least one air-expelling region is based on a desired air pressure within the first chamber. In yet other embodiments, the chamber includes at least one chamfered edge. In various embodiments, the chamber includes a plurality of stitch-through lines, each of the plurality of stitch-through lines coupling the upper layer to the lower layer.

This summary is illustrative only and should not be regarded as limiting.

BRIEF DESCRIPTION OF THE DRAWINGS

The disclosure will become more fully understood from the following detailed description, taken in conjunction with the accompanying figures, wherein like reference numerals refer to like elements, in which:

FIG. 12 is an end view of a dual-chambered patient transfer device, according to an exemplary embodiment.

FIG. 13 is a schematic representation of a side cross-sectional view of the patient transfer device of FIG. 12 taken along line 12-12 of FIG. 12.

FIG. 14 is a top view of the patient transfer device of FIG. 12.

FIG. 15 is a bottom view of the patient transfer device of FIG. 12.

FIG. 16 is a side perspective view of a dual-chambered patient transfer device, according to another exemplary embodiment.

FIG. 17 is an end perspective view of the patient transfer device of FIG. 16.

FIG. 18 is a bottom view of the patient transfer device of FIG. 16.

FIG. 36 is an end view of the patient transfer device of FIG. 34.

FIG. 37 is a side view of the patient transfer device of FIG. 34.

FIG. 38 is a bottom view of the patient transfer device of FIG. 34.

FIG. 69 shows a schematic representation of a perspective view of a patient transfer device having slidably adjustable handles, according to an exemplary embodiment.

FIG. 70 shows a top view of a handle of the patient transfer device of FIG. 69.

FIG. 71 shows a top view of a patient transfer device having a removable strap, according to an exemplary embodiment.

The foregoing and other features of the present disclosure will become apparent from the following description and appended claims, taken in conjunction with the accompanying drawings. Understanding that these drawings depict only several embodiments in accordance with the disclosure and are therefore, not to be considered limiting of its scope, the disclosure will be described with additional specificity and detail through use of the accompanying drawings.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Various patient transfer devices may be used in clinical settings; however, in many cases, these transfer devices are physically demanding on clinical personnel responsible for patient transfer and/or the transfer devices may be uncomfortable for the transferred patient.

Accordingly, it would be advantageous to provide a patient transfer device that reduces physical demand of caregivers and enhances patient comfort.

Figures 1, 2:
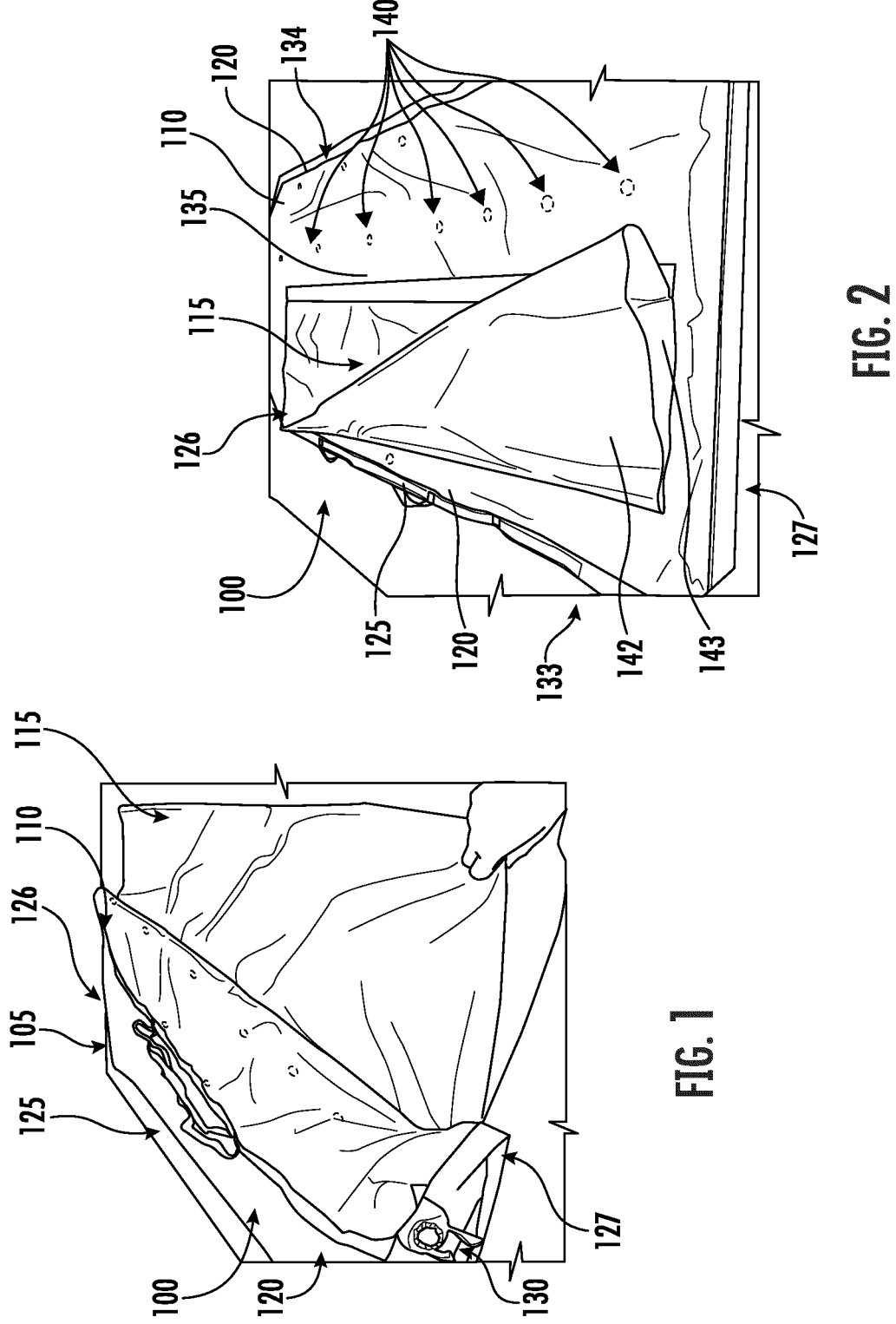
FIG. 1 is a perspective view of a patient transfer device having a slip sheet, illustrating a top and bottom surface of the patient transfer device, according to an exemplary embodiment.
FIG. 2 is an end view of the patient transfer device of FIG. 1 illustrating the bottom surface of the patient transfer device.

Referring to FIGS. 1-2, perspective and bottom views of a patient transfer device 100 are shown, according to an exemplary embodiment. The patient transfer device 100 is configured for facilitating transfer of a patient from a first surface to a second surface. As shown, the patient transfer device 100 includes an upper layer 105 defining an upper surface and a lower layer 110 defining a lower surface. The lower surface is configured to contact a support surface on which the patient transfer device 100 is placed. The upper layer 105 and the lower layer 110 are mutually joined along a shared outer perimeter such that the outer perimeter forms an outer boundary of the patient transfer device 100 defined between a top edge 126, a bottom edge 127, a first side edge 133, and a second side edge 134. Accordingly, the upper layer 105 and the lower layer 110 form a chamber therebetween. The patient transfer device 100 includes a slip sheet 115, which is coupled to the lower layer 110.

As shown, the patient transfer device 100 includes a plurality of handles 120 disposed along the outer perimeter of the patient transfer device 100. Although FIG. 1 shows the handles 120 disposed along the outer perimeter on the lower layer 110, the handles 120 may additionally or alternatively be disposed along the outer perimeter on the upper layer 105. The patient transfer device 100 also includes one or more straps 125, which are coupled along the outer perimeter of the patient transfer device 100 and extend outwardly therefrom. In various embodiments, the straps 125 may be configured to support, secure, or maintain the patient transfer device 100 upon the support surface. In various embodiments, the straps 125 may be coupled along the outer perimeter on the lower layer 110, the upper layer 105, or a combination thereof. The patient transfer device 100 may also include a port 130 (e.g., quick connect port), which may be configured for connection to one or more airflow devices to enable inflation and deflation of the patient transfer device 100. In various embodiments, the airflow devices may include, but are not limited to, air pumps, vacuums, compressors, etc.

As described above, the patient transfer device 100 is configured to facilitate transfer of a patient from a first surface to a second surface. Transfer of the patient by the patient transfer device 100 is enabled by sliding of the slip sheet 115. As shown in FIG. 2, the slip sheet 115 is coupled to the lower layer 110 along a line 135, which extends longitudinally along the lower layer 110. In various embodiments, the line 135 may be stitched, adhered, integrally formed, etc. As illustrated in FIG. 2, the slip sheet 115 forms a loop or channel such that the slip sheet 115 has a first side 142, which is disposed to contact the support surface on which the patient transfer device 100 is placed. The loop or channel formed by the slip sheet 115 is configured such that a second side 143, opposite the first side 142, is disposed to be in contact with itself. In various embodiments, the slip sheet 115 is made of a low-friction material (e.g., a material having a lower friction coefficient as compared to the lower layer 110). In various embodiments, the first side 142 of the slip sheet 115 has a greater coefficient of friction than the second side 143.

During use, the patient transfer device 100 may be placed upon a first surface (e.g., support surface) such that the lower layer 110 is disposed adjacent the first surface. The patient transfer device 100 may be subsequently inflated (i.e., via an airflow device connected to the port 130). To transfer a patient, the handles 120 and/or straps 125 may be used to pull the patient transfer device 100 in a transverse direction (i.e., in a direction substantially perpendicular to first and/or second side edges 133, 134). As the patient transfer device 100 is pulled, the slip sheet 115 may facilitate ease of movement of the patient transfer device 100 as the second side 143 of the slip sheet 115 slides against itself, thereby reducing a force needed to pull the patient transfer device 100.

In various embodiments, the patient transfer device 100 may include one or more regions 140 disposed along the lower layer 110 having stitching or features configured to further reduce a pull force on the patient transfer device 100. In various embodiments, the regions 140 may include one or more through stitches. The through stitches are configured to reduce a surface area of the lower layer 110 disposed to contact the support surface on which the patient transfer device 100 is placed. In various embodiments, the regions 140 may include one or more apertures disposed within the lower layer 110 such that air flowing within the patient transfer device 100 (i.e., air flow within the chamber formed by the upper and lower layers 105, 110) may be expelled through the regions 140 and consequently reduce an amount of friction between the lower layer 110 and the support surface on which the patient transfer device 100 is placed.

Figure 3:
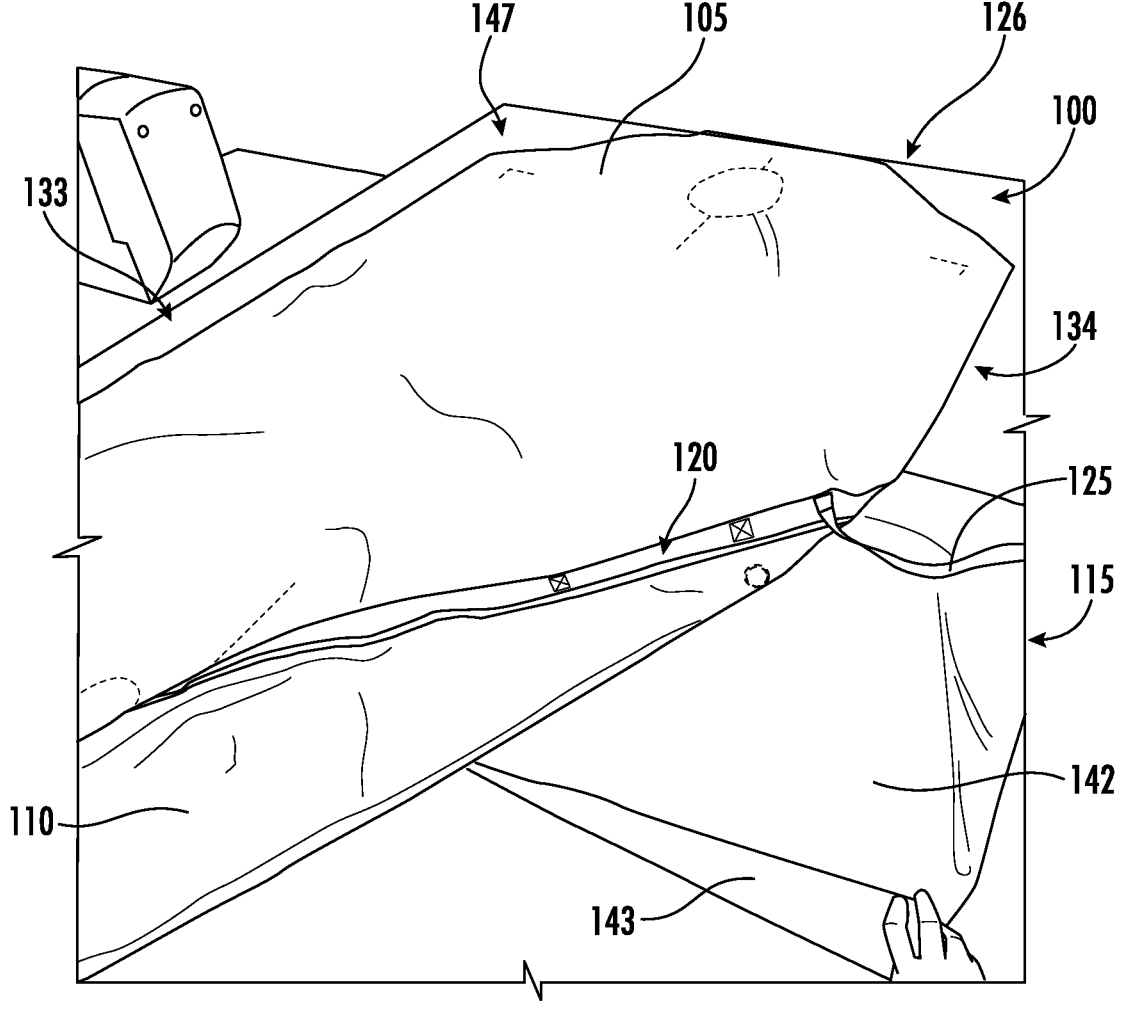
FIG. 3 is a perspective view of a patient transfer device of having a slip sheet, according to another exemplary embodiment.

In various embodiments, the patient transfer device 100 may have varying lengths of the slip sheet 115. As shown in FIG. 1-2, the slip sheet 115 may be configured to extend substantially along a length of the patient transfer device in a direction substantially parallel to the first and second side edges 133, 134. Alternatively, as shown in FIG. 3, the slip sheet 115 may extend along only a portion of the length of the patient transfer device 100 in a direction substantially parallel to the first and second side edges 133, 134. In various embodiments, the slip sheet 115 may be coupled to the lower layer 110 in a substantially central position relative to each of the top edge 126, bottom edge 127, first side edge 133, and second side edge 134. In various embodiments, the slip sheet 115 may be coupled to the lower layer 110 at any position thereon, which is bounded by the outer perimeter of the patient transfer device 100. In various embodiments, the slip sheet 115 may be removably coupled to the lower layer 110 such that the slip sheet 115 may be coupled to the lower layer 110 at a position and in an orientation corresponding with a direction of pull on the patient transfer device 100. In various embodiments, the slip sheet 115 may be removably coupled to the lower layer 110 using any suitable method including, but not limited to, hook and loop couplings, snaps, magnets, etc.

In various embodiments, the patient transfer device 100 may be have a substantially rectangular shape. In other embodiments, the patient transfer device 100 may have an ellipsoidal, square, hexagonal, or any polygonal or other shape suitable for facilitating patient transfer.

Figures 4, 5, 6:
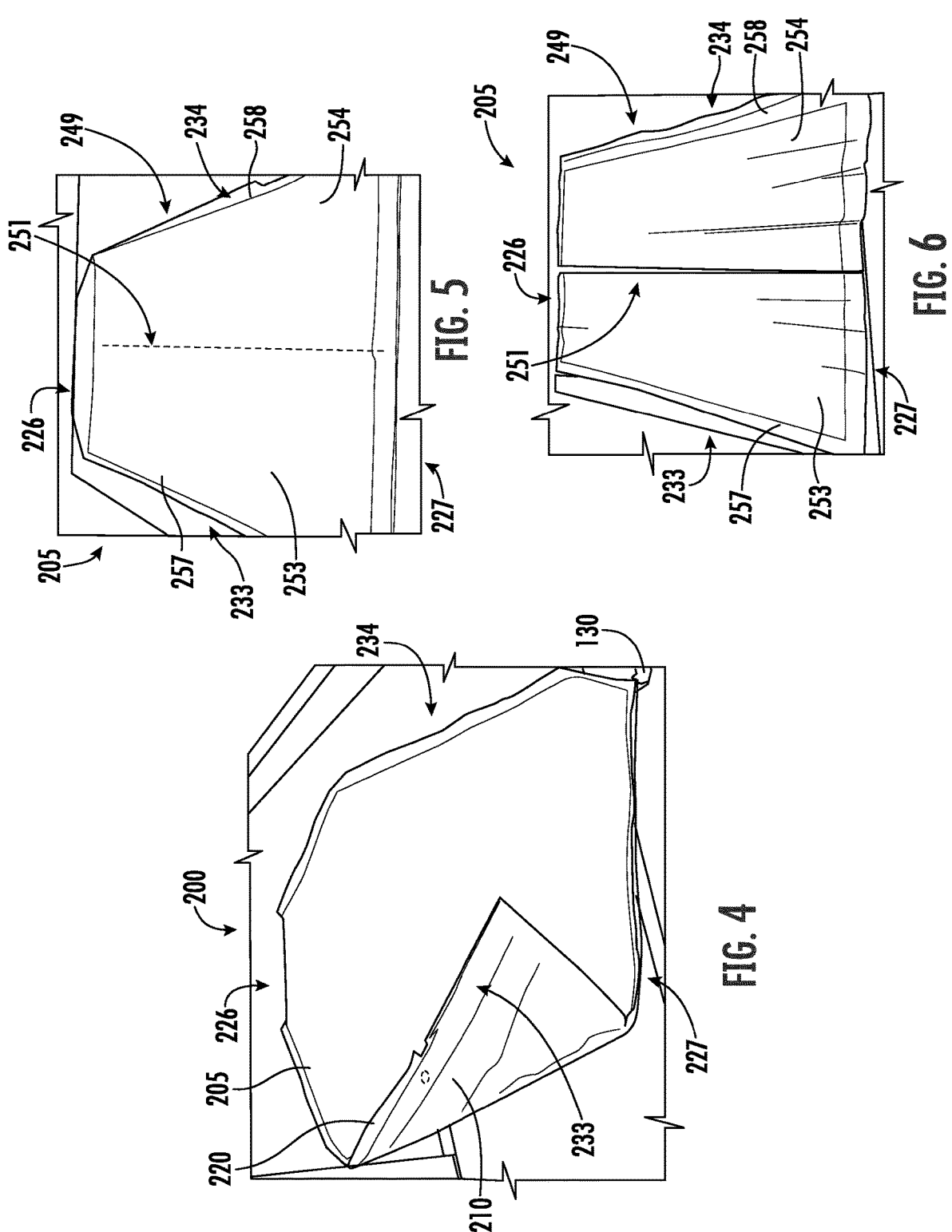
FIG. 4 is a perspective view of a patient transfer device having an absorbent pad, according to an exemplary embodiment.
FIG. 5 is an end view of a top portion of the patient transfer device of FIG. 4.
FIG. 6 is an end view of the top portion of the patient transfer device of FIG. 4 illustrating separation of said top portion.

FIG. 4 shows a perspective view of a patient transfer device 200, according to an exemplary embodiment. The patient transfer device 200 is configured for facilitating transfer of a patient from a first surface to a second surface. As shown, the patient transfer device 200 includes an upper layer 205 defining an upper surface and a lower layer 210 defining a lower surface. The upper layer 205 and the lower layer 210 are mutually joined along a shared outer perimeter such that the outer perimeter forms an outer boundary of the patient transfer device 200 defined between a top edge 226, a bottom edge 227, a first side edge 233, and a second side edge 234. Accordingly, the upper layer 205 and the lower layer 210 form a chamber therebetween.

As shown, the patient transfer device 200 includes a plurality of handles 220 disposed along the outer perimeter of the patient transfer device 200. Although FIG. 4 shows the handles 220 disposed along the outer perimeter on the lower layer 210, the handles 220 may additionally or alternatively be disposed along the outer perimeter on the upper layer 205. In various embodiments, the patient transfer device 200 may further include one or more straps, which may be coupled along the outer perimeter of the patient transfer device 200 and extend outwardly therefrom. In various embodiments, the one or more straps may be configured to support, secure, or maintain the patient transfer device 200 upon the support surface. The patient transfer device 200 may also include a port 230 (e.g., quick connect port), which may be configured for connection to one or more airflow devices to enable inflation and deflation of the patient transfer device 200. In various embodiments, the one or more airflow devices may include, but are not limited to, air pumps, vacuums, compressors, etc.

During use, the patient transfer device 200 may become soiled (e.g., by a patient) or otherwise unfit for use to transfer a patient. As shown in FIG. 5, the upper layer 205 of the patient transfer device 200 includes an absorbent pad 249, which is coupled along at least the first and second side edges 233, 234 of the patient transfer device 200. In various embodiments, the absorbent pad 249 may be configured to absorb moisture and fluid (e.g., sweat, incontinence moisture, other bodily fluids) away from a patient being transferred. In various embodiments, the absorbent pad 249 may be a microclimate body pad. In various embodiments, the absorbent pad 249 may be coupled to the upper layer 205 along the top and bottom edges 226, 227, or along the entire outer perimeter of the patient transfer device 200. In various embodiments, the absorbent pad 249 may be coupled using one or more adhesives and/or fasteners.

In various embodiments, the absorbent pad 249 may include a plurality of layers and each layer within the absorbent pad 249 is itself an absorbent pad. In such embodiments, a soiled layer of the absorbent pad 249 may be removed to expose a clean, unsoiled layer. As shown in FIG. 5, the absorbent pad 249 may include a perforation 251, which extends a long a length of the absorbent pad 249. Accordingly, when a layer of the absorbent pad 249 becomes soiled, a first portion 253 of the absorbent pad 249 may be separated from a second portion 254 of the absorbent pad by tearing along the perforation 251, as illustrated in FIG. 6. The first and second portions 253, 254 may then be removed from the patient transfer device 200 along edges 257, 258, respectively, to expose a clean, unsoiled layer of the absorbent pad 249. Accordingly, layers within the absorbent pad 249 may be removed without requiring a patient to be removed from the patient transfer device 200. In various embodiments, the perforation 251 may be disposed within a substantially middle region of the absorbent pad 249 such that a perpendicular distance between the perforation 251 and each of the first and second side edges 233, 234 is approximately the same.

Figures 7, 8:
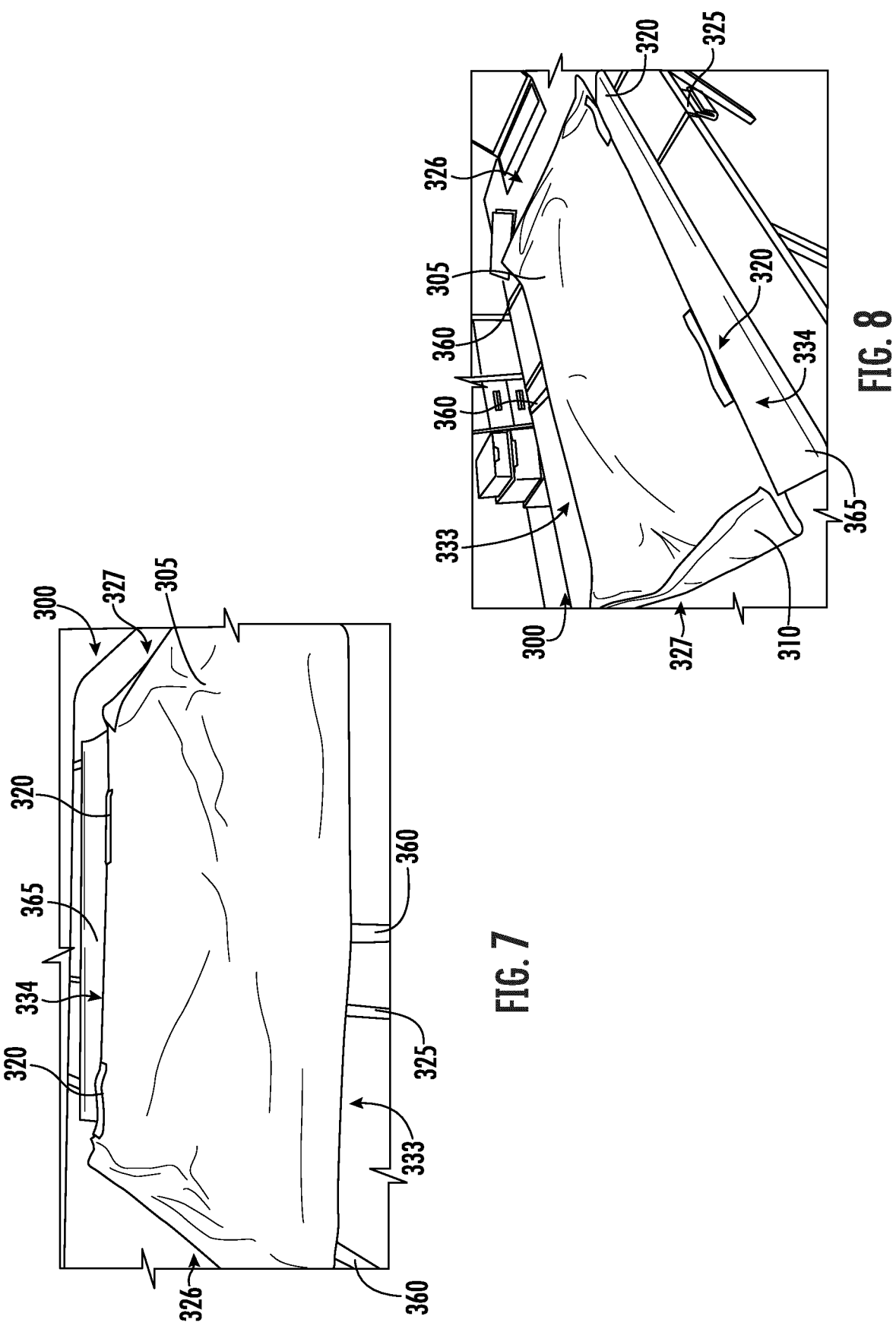
FIG. 7 is a side perspective view of an airless patient transfer device, according to an exemplary embodiment.
FIG. 8 is an end perspective view of the patient transfer device of FIG. 7.

FIGS. 7 and 8 show side and perspective views, respectively, of a patient transfer device 300, according to an exemplary embodiment. The patient transfer device 300 is configured for facilitating transfer of a patient from a first surface to a second surface. As shown, the patient transfer device 300 includes an upper layer 305 defining an upper surface and a lower layer 310 defining a lower surface. The upper layer 305 and the lower layer 310 are mutually joined along a top edge 326 and a bottom edge 327. As illustrated in each of FIGS. 7 and 8, the patient transfer device 300 further includes an intermediate layer 365, which is disposed between the upper layer 305 and the lower layer 310, and between the lower layer 310 and a surface on which the patient transfer device 300 is resting.

As shown, the patient transfer device 300 includes a plurality of handles 320 disposed along a first side edge 333 of the patient transfer device 300. Although FIGS. 7 and 8 show patient transfer device 300 including only the handles 320, the patient transfer device 300 may include any number of handles 320. Although FIGS. 7 and 8 show the patient transfer device 300 having handles 320 disposed along the first side edge 333, various embodiments of the patient transfer device 300 may additionally or alternatively include handles 320 disposed along a second side edge 334. In various embodiments, the patient transfer device 300 may further include one or more straps 325 and/or loops 360, which may be coupled along the outer perimeter of the patient transfer device 300 and extend outwardly therefrom. In various embodiments, the one or more straps 325 and/or loops 360 may be configured to support, secure, or maintain the patient transfer device 300 upon the support surface.

Figure 10:
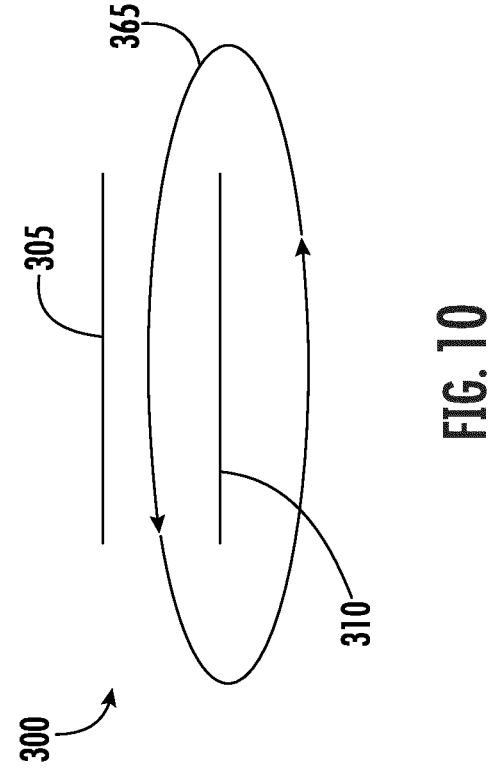
FIG. 10 is a schematic representation of an end cross-sectional view of the patient transfer device of FIG. 7 taken along line 9-9 of FIG. 9.
Figure 9:
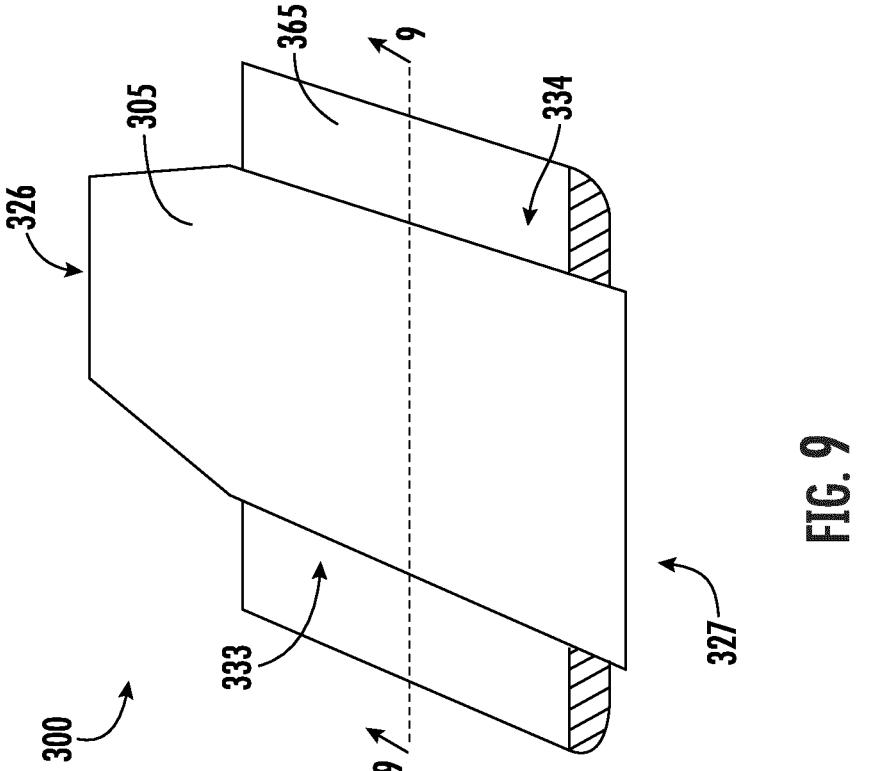
FIG. 9 is a schematic representation of a top view of the patient transfer device of FIG. 7.
Figure 11:
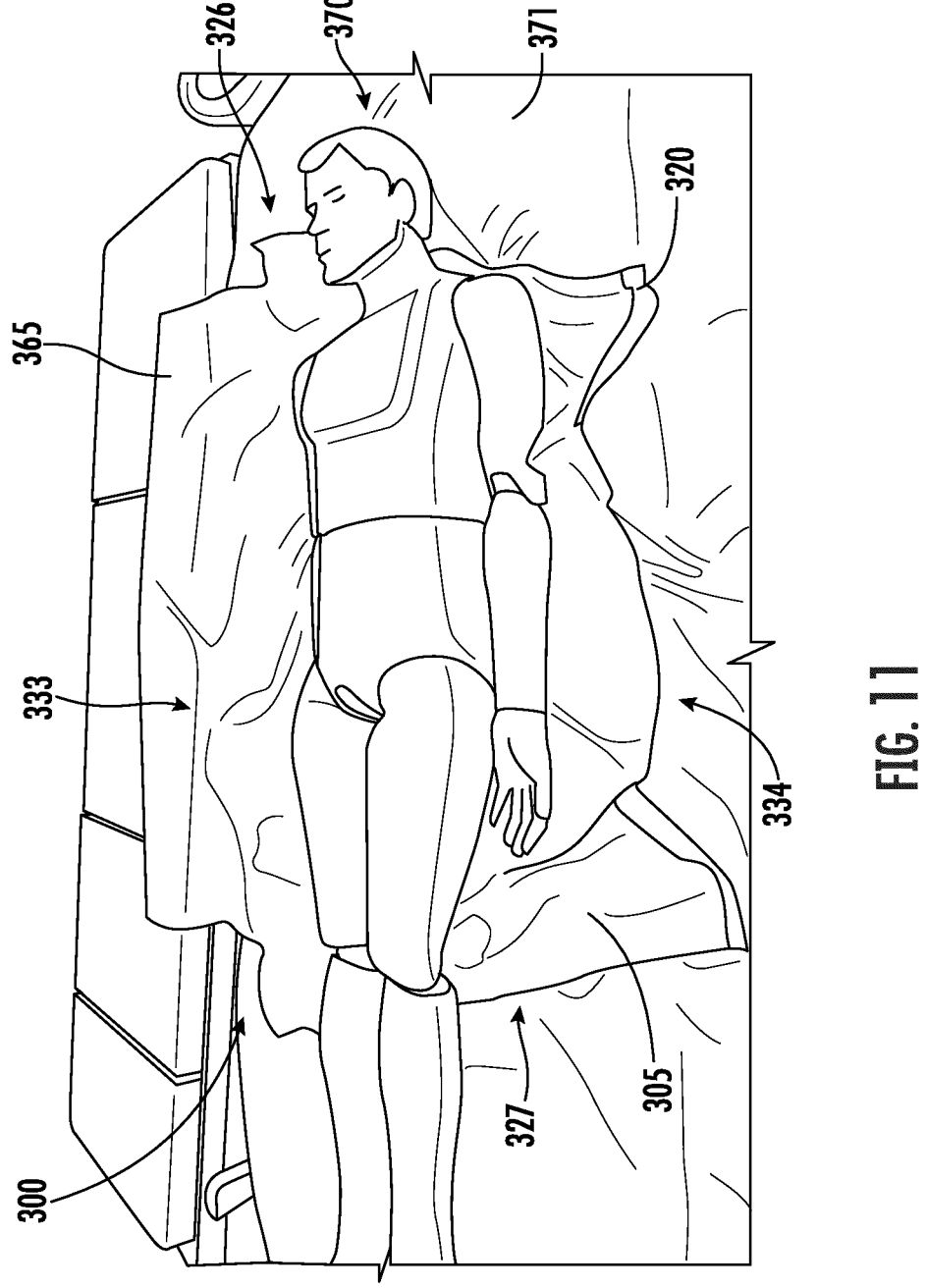
FIG. 11 is a top view of the patient transfer device of FIG. 7 in use with a patient.

As illustrated in FIG. 9, the intermediate layer 365 may be configured as a loop, which is configured to extend past the first and second side edges 333, 334 of the upper and lower layers 305, 310. Each of the upper layer 305, lower layer 310, and intermediate layer 365 may consist of one or more low-friction materials. Accordingly, each of the upper layer 305, lower layer 310, and intermediate layer 365 may be configured to slidably engage with each other. FIG. 10, which shows a cross-sectional view of the patient transfer device 300 taken along line 9-9 of FIG. 9, illustrates the loop formed by the intermediate layer 365, which may facilitate movement of the patient transfer device 300. During patient transfer, a patient 371 may be maneuvered atop the patient transfer device 300, which is supported by a surface 370 (e.g., bed) as illustrated in FIG. 11. The patient transfer device 300 may be subsequently pulled using the handles 320. When the patient transfer device 300 is pulled, the intermediate layer 365 may slide relative to each of the upper and lower layers 305, 310 to enable movement of the patient transfer device 300 and reduce a pull force required to cause said movement.

FIG. 12 shows an end view of a patient transfer device 400, according to an exemplary embodiment. The patient transfer device 100 is configured for facilitating transfer of a patient from a first surface to a second surface. As shown, the patient transfer device 400 includes an upper layer 405 defining an upper surface and a lower layer 410 defining a lower surface. The patient transfer device 400 may further include an intermediate layer 447, disposed between the upper and lower layers 405, 410. The upper layer 405, the intermediate layer 447, and the lower layer 410 are mutually joined along a shared outer perimeter. As illustrated in FIG. 13, which shows a side cross-sectional view of the patient transfer device 400 taken along line 12-12 of FIG. 12, the upper layer 405 and the intermediate layer 447 form a first, upper chamber 440, and the lower layer 410 and the intermediate layer form a second, lower chamber 445 (i.e., such that the upper layer 405 forms a top layer).

FIGS. 14 and 15 show top and bottom views, respectively, of the patient transfer device 400, according to an exemplary embodiment. As described above, the upper layer 405, the intermediate layer 447, and the lower layer 410 are mutually joined along a shared outer perimeter, which is defined between a top edge 426, a bottom edge 427, a first side edge 433, and a second side edge 434. The patient transfer device 400 may further include a port 430 (e.g., quick connect port), which is configured for connection to one or more air flow devices (e.g., pump, vacuum, etc.) to inflate and deflate the patient transfer device 400. During use the patient transfer device 400 may be provided with air (i.e., via the port 430) such that each of the upper and lower chambers 440, 445 inflate. As the patient transfer device 400 inflates, the upper and lower chambers 440, 445 will collaboratively inflate to lift a patient positioned atop the patient transfer device 400 in a manner that enhances comfort by providing cushion.

As shown in FIG. 14, the upper layer 405 may include a plurality of stitch portions 450 such that the upper layer 405 is stitched to at least the intermediate layer 447. Such stitch portions 450 may be configured to facilitate air pressure distribution within the upper chamber 440. In various embodiments, the upper layer 405 may include 7 stitch portions 450 (as shown in FIG. 14). In various embodiments, the upper layer 405 may include any number of stitch portions 450. In various embodiments, the stitch portions 450 may be disposed within the upper layer 405 in a pattern and/or at distances to facilitate cradling a patient positioned atop the patient transfer device 400. In some embodiments, the stitch portions 450 may be arranged in parallel rows or columns, in a staggered configuration, or a combination thereof.

As shown in FIG. 15, patient transfer device 400 may include one or more regions 451 disposed along the lower layer 410 having stitching or features configured to reduce a force required to slide the patient transfer device 400 relative to a support surface on which the patient transfer device 400 is placed. In various embodiments, the regions 451 may include one or more through stitches. The through stitches are configured to reduce a surface area of the lower layer 410 disposed to contact the support surface on which the patient transfer device 400 is placed by causing portions of the lower layer 410 to be spaced apart from the support surface. In various embodiments, the regions 451 may include one or more apertures disposed within the lower layer 410 such that air flowing within the patient transfer device 400 (i.e., air within the upper and/or lower chambers 440, 445) may be expelled through the regions 451 and consequently reduce an amount of friction between the lower layer 410 and the support surface on which the patient transfer device 400 is placed.

FIGS. 16 and 17 show side and end views of the patient transfer device 400, according to an exemplary embodiment. As shown, when the patient transfer device 400 is inflated, the upper and lower chambers 440, 445 may lift a patient 470 off a surface 471 such that the patient 470 is cushioned by the patient transfer device 400. Accordingly, the patient 470 may be prevented from potentially uncomfortable contact with stitching (e.g., stitch portions 450). During transfer of the patient 470, air flow through apertures (i.e., air from within the upper and/or lower chambers 440, 445) within the regions 451 disposed on the lower layer 410, such as illustrated in FIG. 18, may reduce an amount of friction between the lower layer 410 and the support surface 471 (e.g., bed) upon which the patient transfer device 400 is placed. As shown, the patient transfer device 400 includes a plurality of handles 420 disposed along the outer perimeter of the patient transfer device 400. Accordingly, patient transfer may be carried out by pulling on the handles 420, wherein an amount of required pull force may be decreased by the air expelled through the regions 451. Although FIGS. 15 and 16 show the handles 420 disposed along the outer perimeter on the lower layer 410, the handles 420 may additionally or alternatively be disposed along the outer perimeter on the upper layer 405. In various embodiments, the patient transfer device 400 may include a one or more straps coupled along the outer perimeter of the patient transfer device 400 and extend outwardly therefrom. In various embodiments, the one or more straps may be configured to support, secure, or maintain the patient transfer device 400 upon the support surface.

Figures 19, 20:
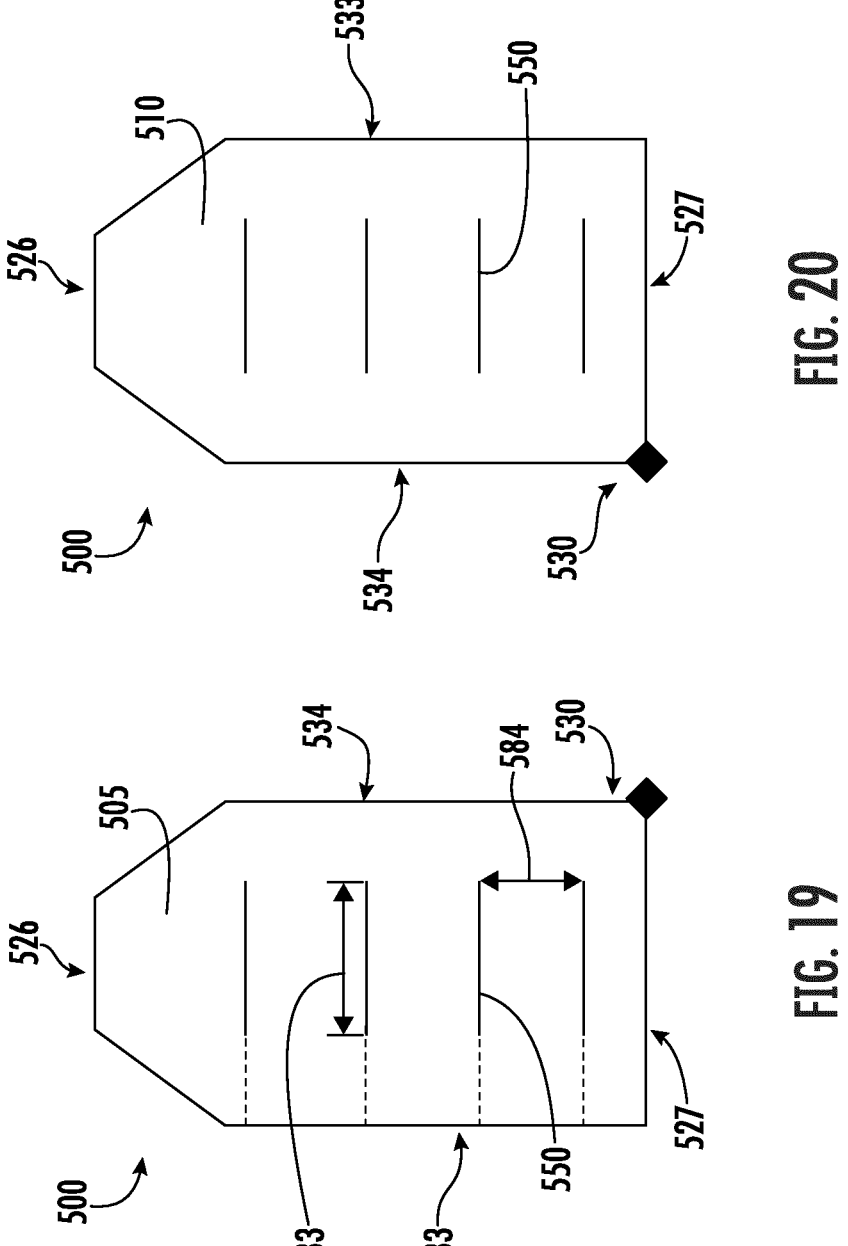
FIG. 19 is a schematic representation of a top view of a patient transfer device having stitch-through lines, according to an exemplary embodiment.
FIG. 20 is a schematic representation of a bottom view of the patient transfer device of FIG. 19.

FIGS. 19 and 20 show schematic representations of top and bottom views, respectively, of a patient transfer device 500, according to an exemplary embodiment. The patient transfer device 500 is configured to facilitate transfer of a patient from a first surface to a second surface. As shown, the patient transfer device 500 includes an upper layer 505 defining an upper surface and a lower layer 510 defining a lower surface. The upper layer 505 and the lower layer 510 are mutually joined along a shared outer perimeter, wherein the outer perimeter forms an outer boundary of the patient transfer device 500 defined between a top edge 526, a bottom edge 527, a first side edge 533, and a second side edge 534. Accordingly, the upper layer 505 and the lower layer 510 form a chamber therebetween.

As shown, the patient transfer device 500 includes a port 530 (e.g., quick connect port), which is configured for connecting to one or more airflow devices (e.g., pump, compressor, vacuum) to inflate and deflate the patient transfer device 500. To facilitate ease of transfer and to enhance patient comfort, the patient transfer device 500 is inflated during use. Furthermore, the patent transfer device 500 may include one or more apertures disposed within the lower layer 510, wherein air entering the patient transfer device 500 (i.e., via the port 530) may be expelled to reduce an amount of friction between the lower layer 510 and a support surface on which the patient transfer device 500 is placed.

To regulate air pressure within the patient transfer device 500 and enable lifting the patient during inflation, the patient transfer device 500 includes a plurality of stitch-through lines 550, as shown in FIGS. 19 and 20. As illustrated, the stitch-through lines 550 may conjoin the upper and lower layers 505, 510 to cause areas of increased pressure within the patient transfer device 500 when inflated, which may provide cushion to a patient. Although FIGS. 19 and 20 show four stitch-through lines 550, various embodiments of the patient transfer device 500 may include any suitable number of stitch-through lines 550. In various embodiments, a length 583 of the stitch-through lines 550 and/or a distance 584 between stitch-through lines 550 may be based on at least one of a desired pressure, cushion, or lift. In various embodiments, the distance 584 may range from approximately 12 inches to approximately 15 inches.

Figures 21, 22, 23:
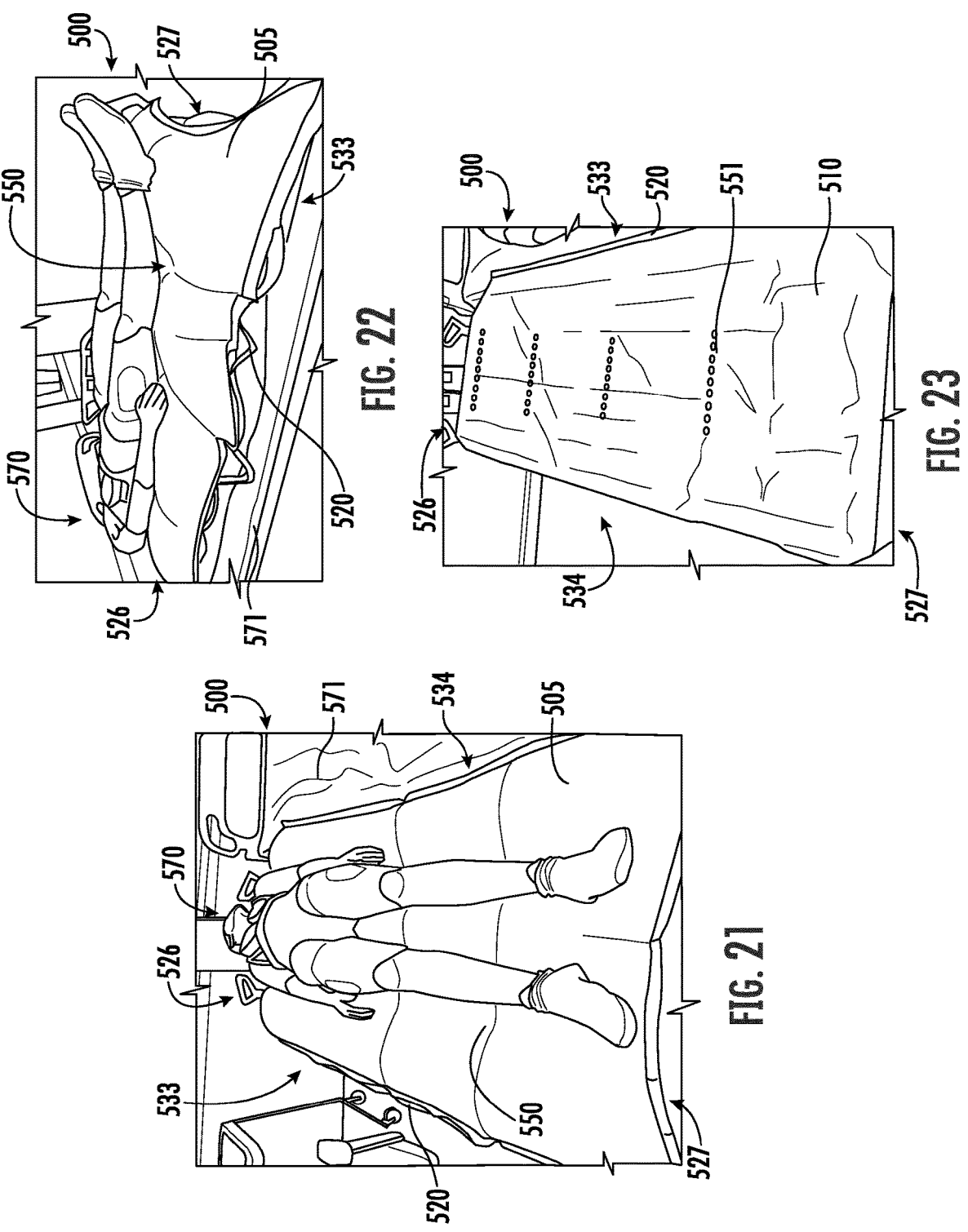
FIG. 21 is an end perspective view of the patient transfer device of FIG. 19.
FIG. 22 is a side view of the patient transfer device of FIG. 19.
FIG. 23 is a bottom view of the patient transfer device of FIG. 19.

FIGS. 21 and 22 show end and side views, respectively, of the patient transfer device 500, according to an exemplary embodiment. As shown, when the patient transfer device 500 is inflated, the patient transfer device 500 may lift a patient 570 off a surface 571 such that the patient 570 is cushioned by the patient transfer device 500. Accordingly, the patient 570 may be prevented from potentially uncomfortable contact with stitching (e.g., stitch-through lines 550). During transfer of the patient 570, air flow through apertures within the regions 551 disposed on the lower layer 510 (i.e., air flow from within the patient transfer device 500), such as illustrated in FIG. 23, may reduce an amount of friction between the lower layer 510 and the support surface 571 upon which the patient transfer device 500 is placed.

As shown, the patient transfer device 500 includes a plurality of handles 520 disposed along the outer perimeter of the patient transfer device 500. Accordingly, patient transfer may be carried out by pulling on the handles 520, wherein an amount of required pull force may be decreased by the air expelled through the regions 551. Although FIG. 22 shows the handles 520 disposed along the outer perimeter on the lower layer 510, the handles 520 may additionally or alternatively be disposed along the outer perimeter on the upper layer 505. In various embodiments, the patient transfer device 500 may include a one or more straps coupled along the outer perimeter of the patient transfer device 500 and extend outwardly therefrom. In various embodiments, the one or more straps may be configured to support, secure, or maintain the patient transfer device 500 upon the support surface.

Figures 24, 25:
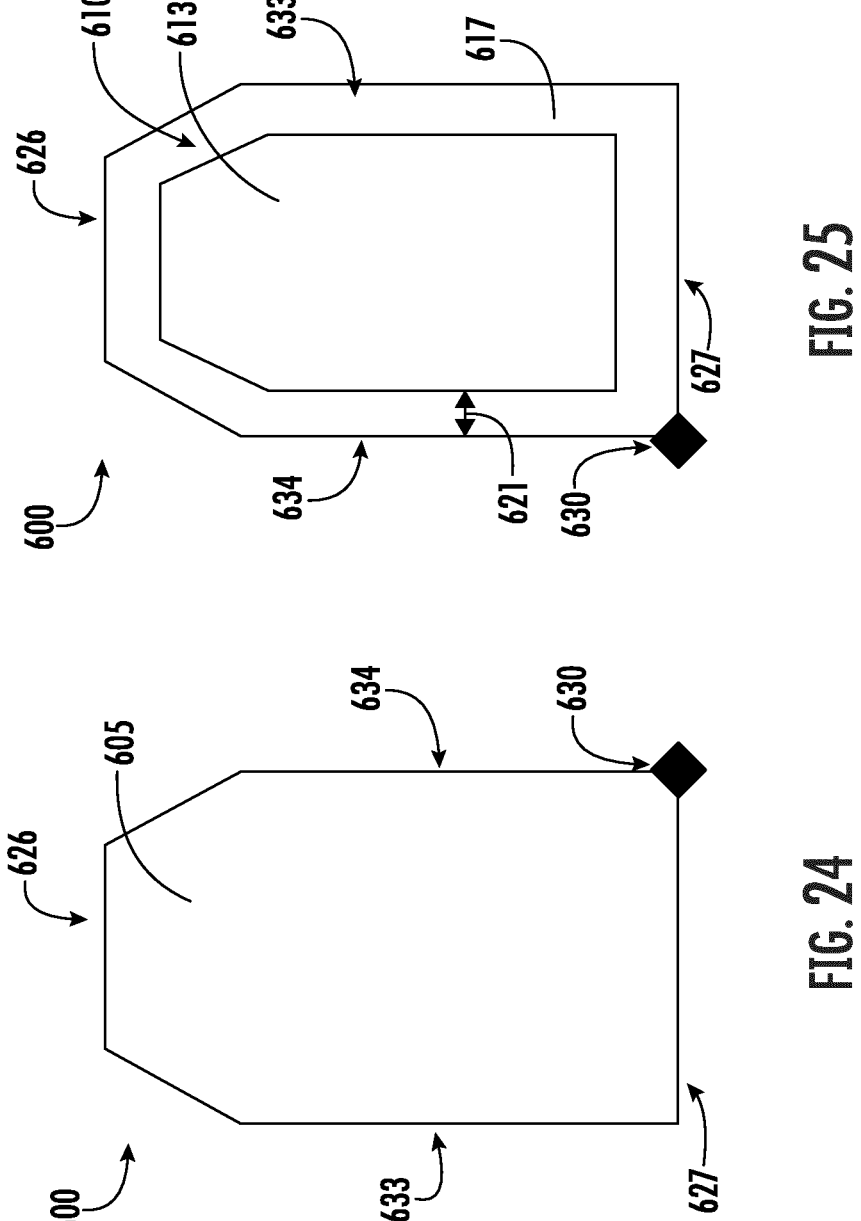
FIG. 24 is a schematic representation of a top view of a ring airflow type patient transfer device, according to an exemplary embodiment.
FIG. 25 is a schematic representation of a bottom view of the patient transfer device of FIG. 24.

In various embodiments, porous materials may be implemented to enable case of patient transfer. FIGS. 24 and 25 show schematic representations of top and bottom views of a patient transfer device 600, according to an exemplary embodiment. The patient transfer device 600 is configured for facilitating transfer of a patient from a first surface to a second surface. As shown, the patient transfer device 600 includes an upper layer 605 defining an upper surface and a lower layer 610 defining a lower surface. The upper layer 605 and the lower layer 610 are mutually joined along a shared outer perimeter, wherein the outer perimeter forms an outer boundary of the patient transfer device 600 defined between a top edge 626, a bottom edge 627, a first side edge 633, and a second side edge 634. Accordingly, the upper layer 605 and the lower layer 610 form a chamber therebetween. The patient transfer device 600 may also include a port 630 (e.g., quick connect port), which may be configured for connection to one or more airflow devices to enable inflation and deflation of the patient transfer device 600. In various embodiments, the one or more airflow devices may include, but are not limited to, air pumps, vacuums, compressors, etc.

As shown in FIG. 25, the lower layer 610 includes a non-porous portion 613 and a porous portion 617. The porous portion 617 forms an outer region of the lower layer 610, which surrounds the non-porous portion 613, which forms an inner region of the lower layer 610. Accordingly, when the patient transfer device 600 is inflated (i.e., provided with air via the port 630), air may be expelled through pores within the porous portion 617. Air expelled through the porous portion 617 may reduce a coefficient of friction between the lower layer 610 and a support surface (i.e., by reducing an amount of contact therebetween) upon which the patient transfer device 600 is placed, thereby facilitating case of sliding of the patient transfer device 600. In various embodiments, a width 621 of the porous portion 617 may be variable depending a on a desired amount of airflow through the patient transfer device 600. In various embodiments, the width 621 of the porous portion 617 may range from approximately 1 inch to approximately 3 inches. In various embodiments, the width 621 may be determined based on at least one of a length (e.g., distance between top and bottom edges 626, 627) or a width (e.g., distance between first and second side edge 633, 634) of the patient transfer device 600. In various embodiments, the length of the patient transfer device 600 may be approximately 89 inches and a width of the patient transfer device 600 may be approximately 47 inches. In various embodiments, a size of the pores within the porous portion 617 may be based on or optimized to accommodate a preferred air flow rate through the air transfer device 600 (i.e., within the chamber formed by the upper and lower layers 605, 610).

Figures 26, 27:
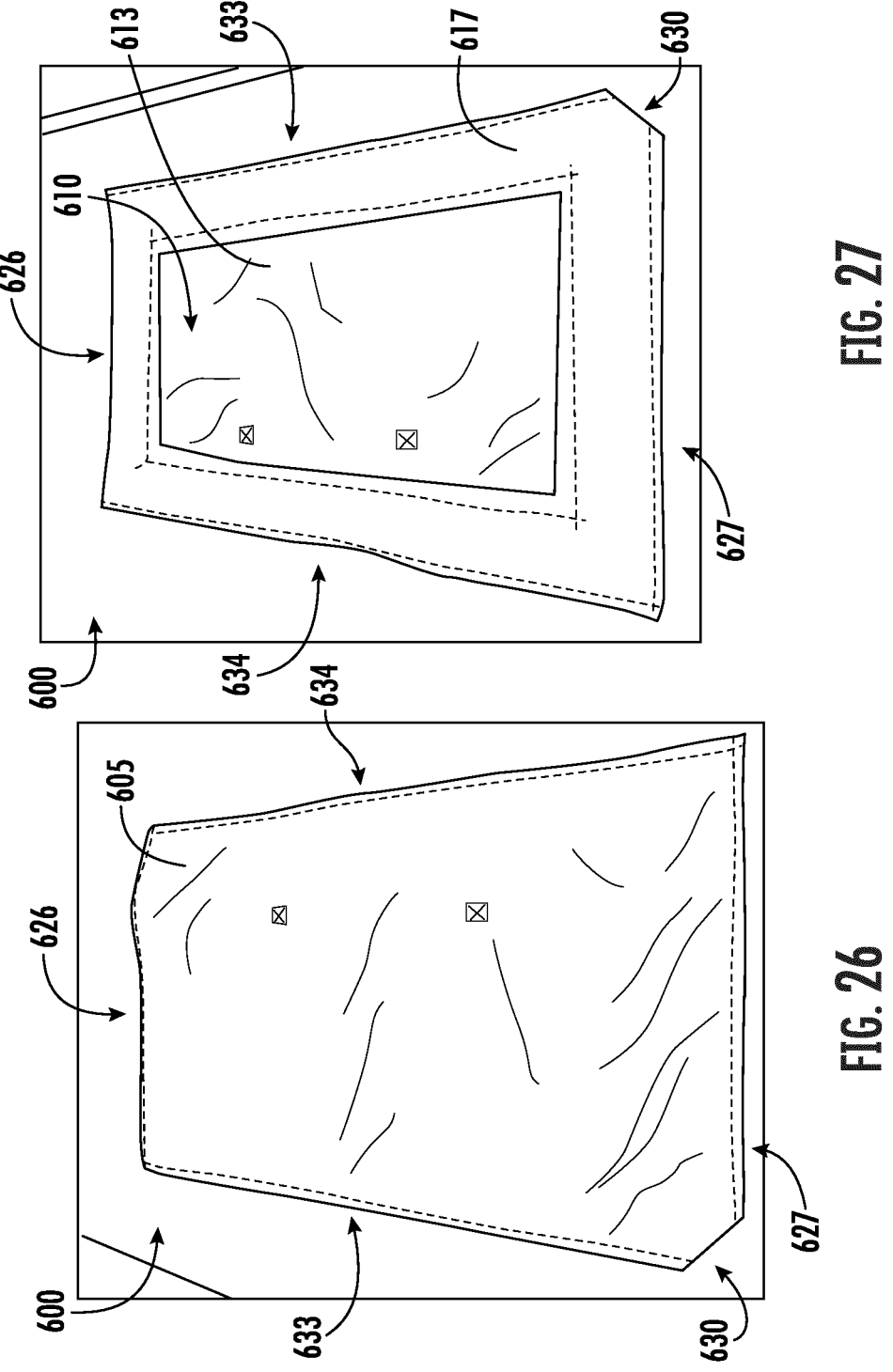
FIG. 26 a top view of the patient transfer device of FIG. 24.
FIG. 27 is a bottom view of the patient transfer device of FIG. 24.

In various embodiments, the patient transfer device 600 may have angled or chamfered edges, such as shown in FIGS. 24 and 25. In other embodiments, the patient transfer device 600 may have a generally rectangular shape, as illustrated in FIGS. 26 and 27.

Figure 29:
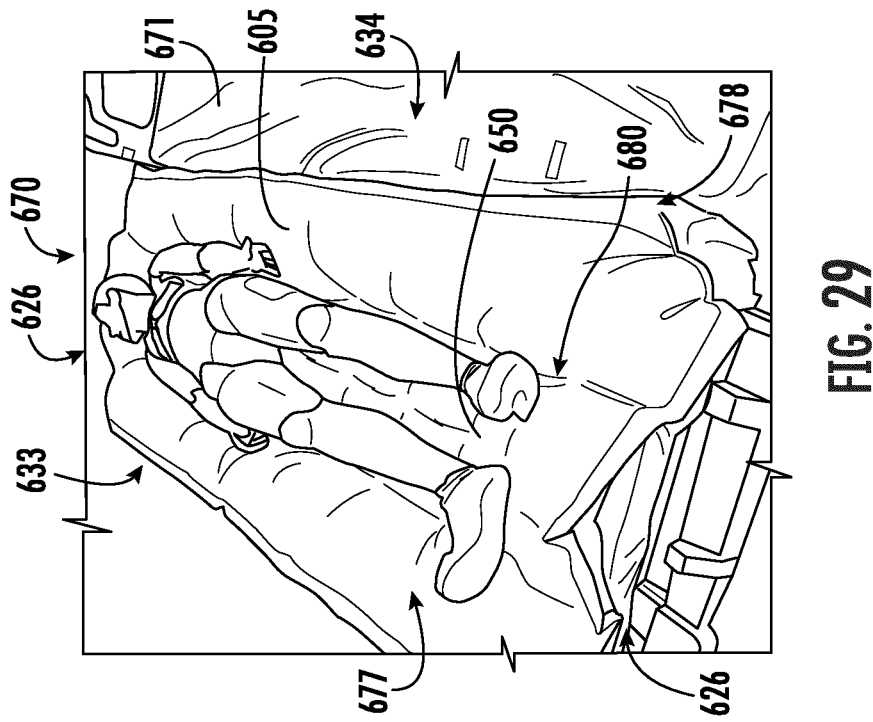
FIG. 29 is an end view of the patient transfer device of FIG. 28.
Figure 28:
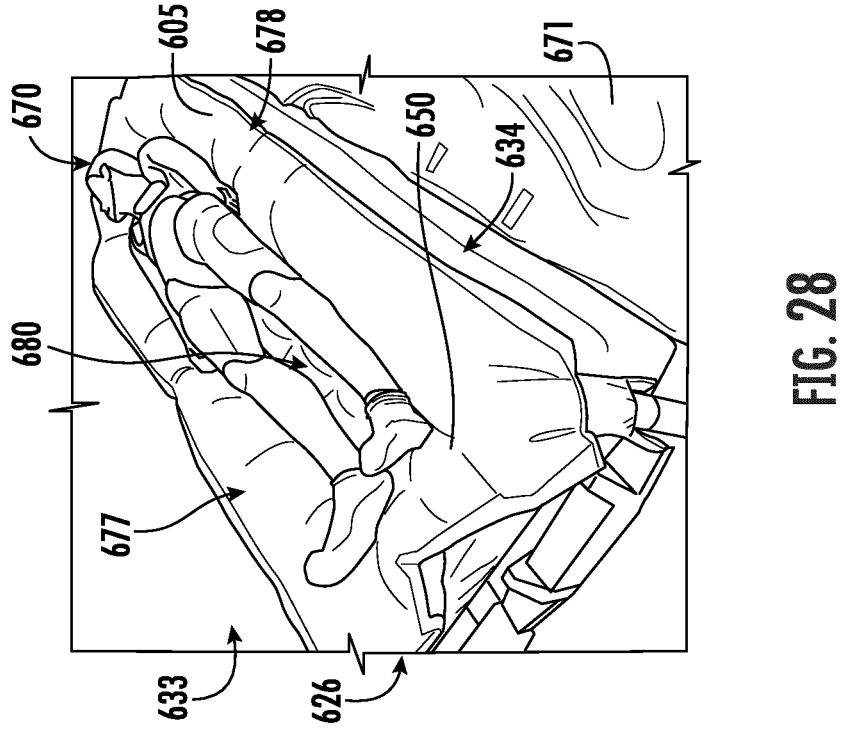
FIG. 28 is a perspective view of a ring airflow type patient transfer device, according to an exemplary embodiment.

In various embodiments, the patient transfer device 600 includes a plurality of stitch portions 650, as shown in FIGS. 28 and 29, wherein the upper layer 605 is stitched to the lower layer 610. Such stitch portions 650 may be configured to facilitate air pressure distribution within the patient transfer device 600. In various embodiments, the patient transfer device 600 may include 19 stitch portions 650 (as shown in FIGS. 28 and 29). In various embodiments, the patient transfer device 600 may include any number of stitch portions 650. In various embodiments, the stitch portions 650 may be disposed in a pattern and/or at distances to facilitate cradling a patient 670 positioned atop the patient transfer device 600, which is disposed on a surface 671. As shown in FIGS. 26 and 27, the stitch portions 650 may cause the patient transfer device 600 to form a cradle surrounding the patient 670 by forming a recessed region 680 disposed between raised regions 677 and 678, wherein the raised regions 677 and 678 support opposite sides of the patient 670. Accordingly, the recessed region 680 and the raised regions 677, 678 may enhance comfort and security of the patient 670 during sliding of the patient transfer device 600 (i.e., during transfer of the patient 670).

In various embodiments, the patient transfer device 600 may include one or more handles disposed along the outer perimeter of the patient transfer device 600. In various embodiments, the one or more handles may be coupled along the outer perimeter on the lower layer 610 and/or on the upper layer 605. In some embodiments, the patient transfer device 600 may also include one or more straps, which may be coupled along the outer perimeter of the patient transfer device 600 and may extend outwardly therefrom. In various embodiments, the one or more straps may be configured to support, secure, or maintain the patient transfer device 600 upon the support surface.

Figures 30, 31:
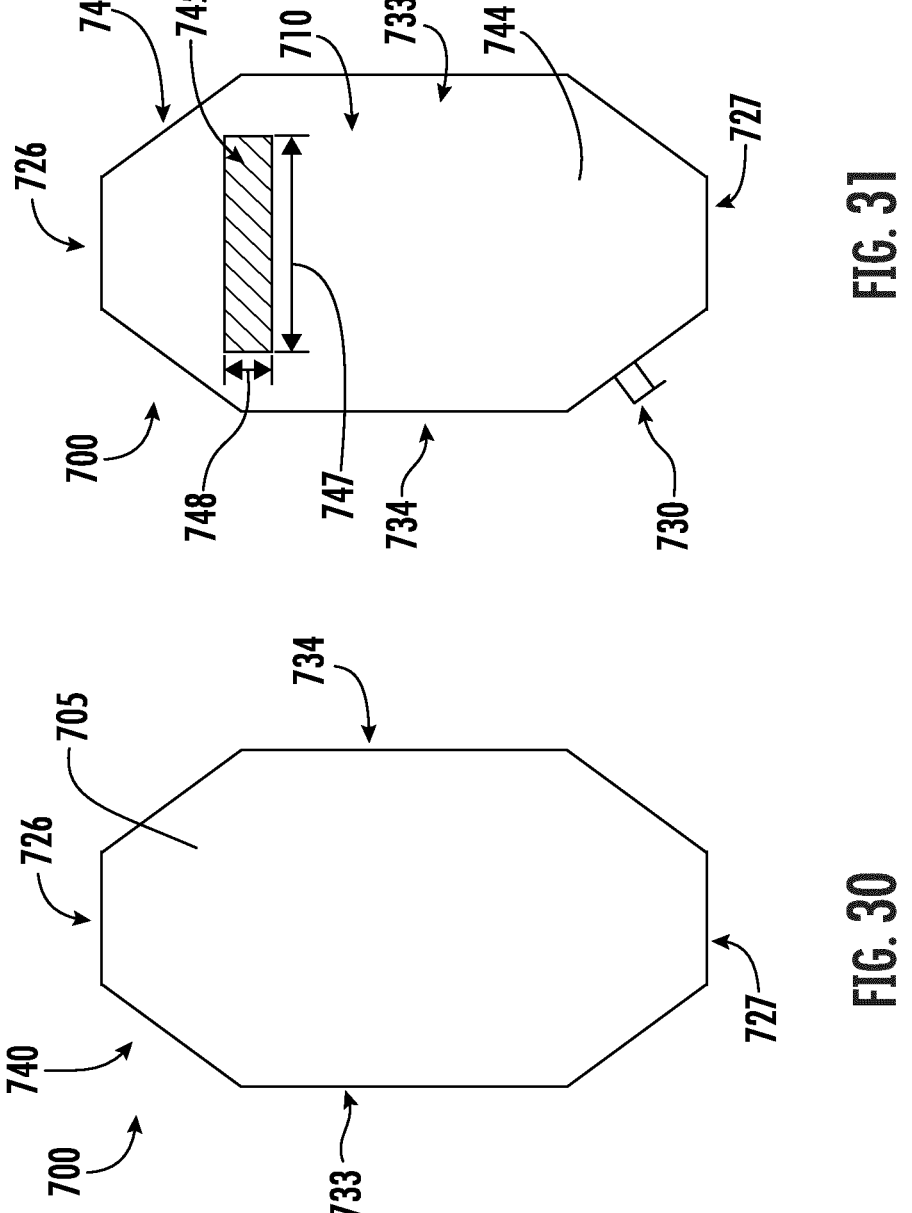
FIG. 30 is a schematic representation of a top view of a patient transfer device with a porous strip, according to an exemplary embodiment.
FIG. 31 is a schematic representation of a bottom view of the patient transfer device of FIG. 30.

In various embodiments, a porous strips may be implemented to facilitate ease of movement or sliding of a patient transfer device. FIGS. 30 and 31 show schematic representations of top and bottom views, respectively, of a patient transfer device 700, according to an exemplary embodiment. The patient transfer device 700 is configured for facilitating transfer of a patient from a first surface to a second surface. As shown, the patient transfer device 700 includes an upper layer 705 defining an upper surface and a lower layer 710 defining a lower surface. The upper layer 705 and the lower layer 710 are mutually joined along a shared outer perimeter, wherein the outer perimeter forms an outer boundary of the patient transfer device 700 defined between a top edge 726, a bottom edge 727, a first side edge 733, and a second side edge 734. Accordingly, the upper layer 705 and the lower layer 710 form a chamber therebetween. The patient transfer device 700 may also include a port 730 (e.g., quick connect port), which may be configured for connection to one or more airflow devices to enable inflation and deflation of the patient transfer device 700. In various embodiments, the one or more airflow devices may include, but are not limited to, air pumps, vacuums, compressors, etc.

As shown in FIG. 31, the lower layer 710 includes a non-porous portion 744 and a porous portion 745. The porous portion 745 forms a strip transversely disposed across the lower layer 710 (i.e., extending in a direction substantially perpendicular to the first and second side edges 733, 734) and is surrounded by the non-porous portion 744. Accordingly, when the patient transfer device 700 is inflated (i.e., provided with air via the port 730), air may be expelled through pores within the porous portion 745. Air expelled through the porous portion 745 may reduce a coefficient of friction between the lower layer 710 and a support surface (i.e., by reducing an amount of contact therebetween) upon which the patient transfer device 700 is placed, thereby facilitating case of sliding of the patient transfer device 700. In various embodiments, at least one of a length 747 or a width 748 of the porous portion 745 may be variable depending a on a desired amount of airflow through the patient transfer device 700. In various embodiments, the length 747 of the porous portion 745 may be approximately 15 inches. In various embodiments, the width 748 of the porous portion 745 may range from approximately 1 inch to approximately 4 inches. In various embodiments, the length 747 and/or width 748 may be determined based on at least one of a length (e.g., distance between top and bottom edges 726, 727) or a width (e.g., distance between first and second side edge 733, 734) of the patient transfer device 700. In various embodiments, the length of the patient transfer device 700 may be approximately 89 inches and a width of the patient transfer device 700 may be approximately 47 inches. In various embodiments, a size of the pores within the porous portion 745 may be based on or optimized to accommodate a preferred air flow rate through the air transfer device 700 (i.e., within the chamber formed by the upper and lower layers 705, 710).

In various embodiments, the patient transfer device 700 may have angled or chamfered edges 740, such as those shown in FIGS. 30 and 31. As illustrated, the chamfered edges 740 may be disposed between the top edge 726 and each of the first and second side edges 733 and 734, and between the bottom edge 727 and each of the first and second side edges 733 and 734. The chamfered edges 740 may be configured to enable more air pressure to be maintained within the patient transfer device 700 as compared to an amount of air pressure if the patient transfer device 700 was rectangular. In some embodiments, the chamfered edges 740 may have a length and/or height based on or optimized to accommodate a preferred air flow rate and/or air pressure within the air transfer device 700. In some embodiments, the height of the chamfered edges 740 may be approximately 12 inches. In some embodiments, a length of each of the top and bottom edges 726, 727 is approximately 29 inches.

Figure 33:
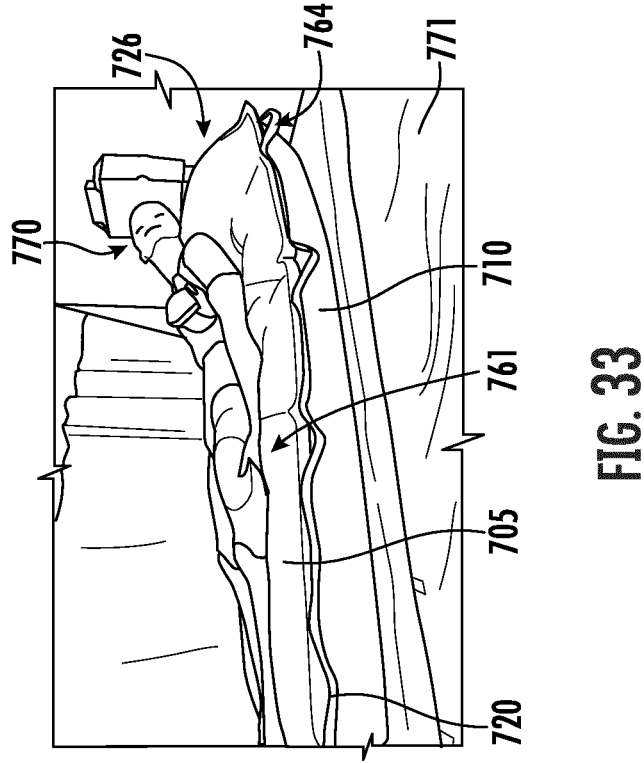
FIG. 33 is a side view of the patient transfer device of FIG. 30.
Figure 32:
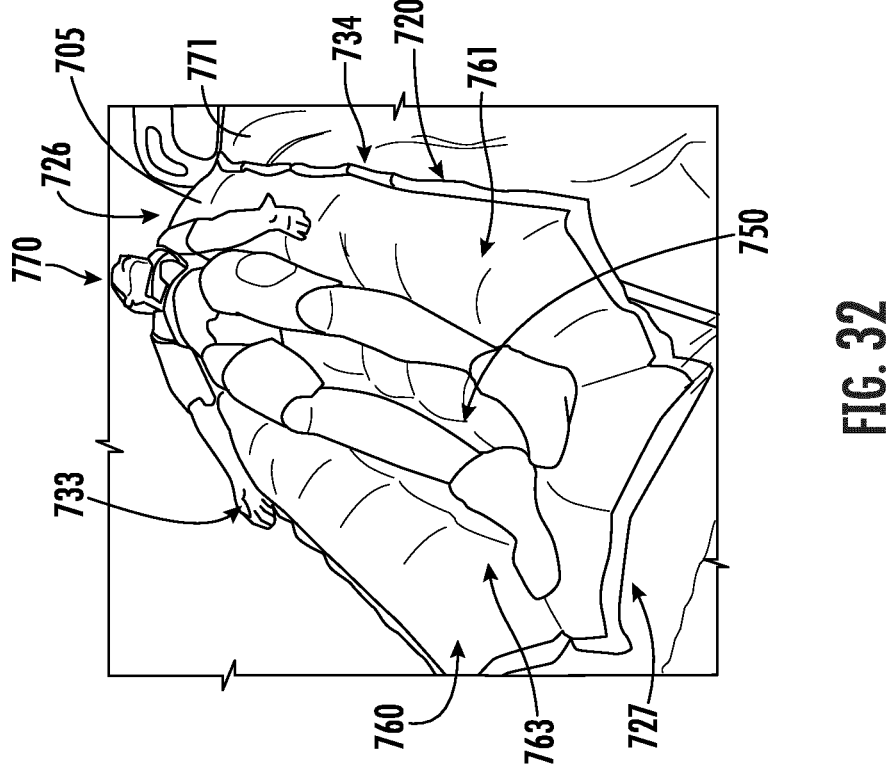
FIG. 32 is an end view of the patient transfer device of FIG. 30.

In various embodiments, the patient transfer device 700 includes a plurality of stitch portions 750, as shown in FIGS. 32 and 33, wherein the upper layer 705 is stitched to the lower layer 710. Such stitch portions 750 may be configured to facilitate air pressure distribution within the patient transfer device 700. In various embodiments, the patient transfer device 700 may include any number of stitch portions 750 (e.g., 4, 6, 12, 19, etc.). In various embodiments, the stitch portions 750 may be disposed in a pattern and/or at distances to facilitate cradling a patient 770 positioned atop the patient transfer device 700, which is disposed on a surface 771 (e.g., bed). As shown in FIGS. 32 and 33, the stitch portions 750 may cause the patient transfer device 700 to form a cradle surrounding the patient 770 by forming a recessed region 763 disposed between raised regions 760 and 761, wherein the raised regions 760 and 761 support opposite sides of the patient 770. Accordingly, the recessed region 763 and the raised regions 760, 761 may enhance patient comfort and security during sliding of the patient transfer device 700 (i.e., during transfer of the patient 770).

As shown in FIGS. 32 and 33, the patient transfer device 700 may include one or more handles 720 disposed along the outer perimeter of the patient transfer device 700. In various embodiments, the one or more handles 720 may be coupled along the outer perimeter on the lower layer 710 and/or on the upper layer 705. In some embodiments, the patient transfer device 700 may also include one or more straps, which may be coupled along the outer perimeter of the patient transfer device 700 and may extend outwardly therefrom. In various embodiments, the one or more straps may be configured to support, secure, or maintain the patient transfer device 700 upon the support surface.

Figures 34, 35:
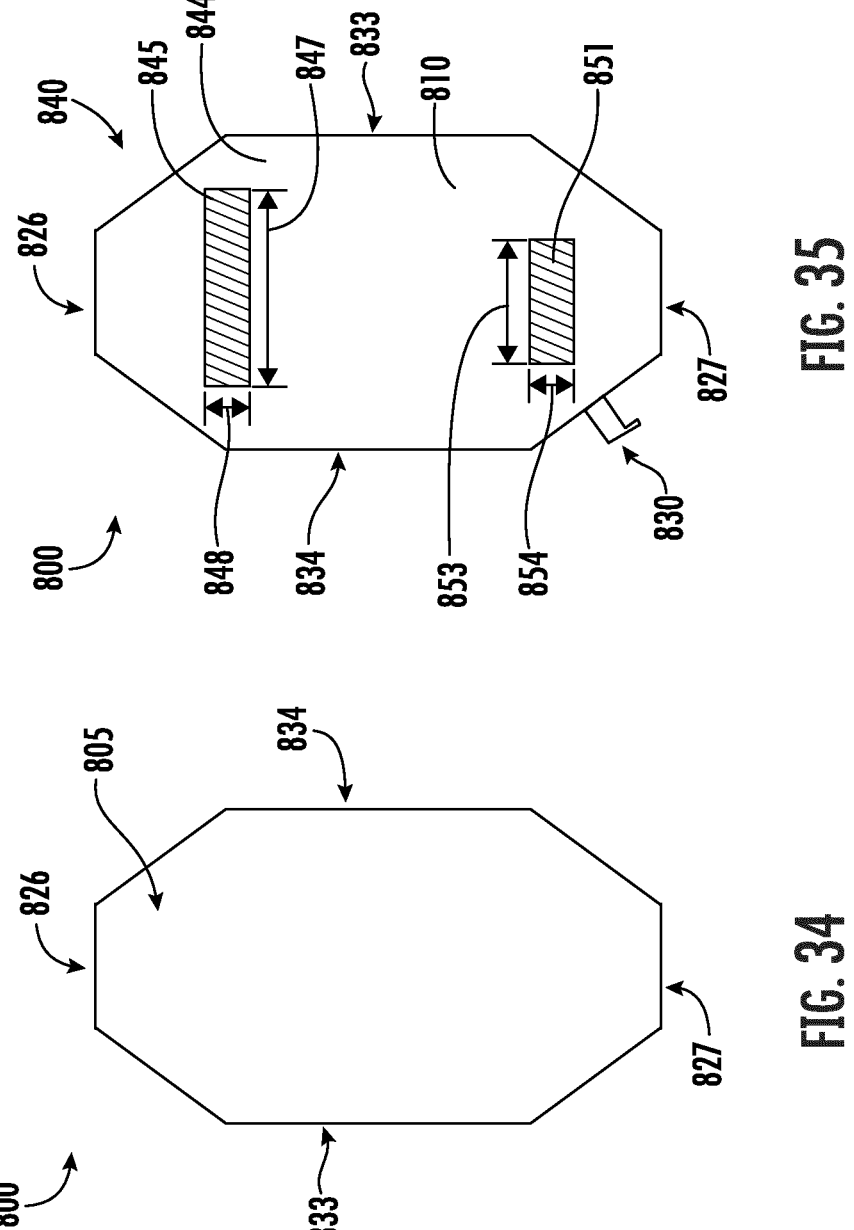
FIG. 34 is a schematic representation of a top view of a patient transfer device having multiple porous strips, according to an exemplary embodiment.
FIG. 35 is a schematic representation of a bottom view of the patient transfer device of FIG. 34.

In some embodiments, a patient transfer device may include a plurality of porous portions to facilitate airflow and ease sliding of the device during patient transfer. FIGS. 34 and 35 show schematic representations of top and bottom views, respectively, of a patient transfer device 800, according to an exemplary embodiment. The patient transfer device 800 is configured for facilitating transfer of a patient from a first surface to a second surface. In various embodiments, features 805-848 of the patient transfer device 800 are similar or equivalent to features 705-748 of the patient transfer device 700.

As shown in FIG. 35, the lower layer 810 includes the non-porous portion 844 and two porous portion 845 and 851.

As shown, each the porous portions 845, 851 forms a strip transversely disposed across the lower layer 810 (i.e., extending in a direction substantially perpendicular to the first and second side edges 833, 834) and is surrounded by the non-porous portion 844. Accordingly, when the patient transfer device 800 is inflated (i.e., provided with air via the port 830), air may be expelled through pores within each of the porous portions 845, 851. Air expelled through the porous portions 845, 851 may consequently reduce a coefficient of friction between the lower layer 810 and a support surface (i.e., by reducing an amount of contact therebetween) upon which the patient transfer device 800 is placed, thereby facilitating case of sliding of the patient transfer device 800 (and facilitating a reduced demand in load from medical personnel transferring the patient). In various embodiments, at least one of the length 847 or the width 848 of the porous portion 845, and/or at least one of a length 853 or width 854 of the porous portion 851 may be variable depending a on a desired amount of airflow through the patient transfer device 800. In various embodiments, at least one of the length 847 or the length 853 may be approximately 15 inches. In various embodiments, at least one of the width 848 or the width 854 may range from approximately 1 inch to approximately 3 inches. In various embodiments, the lengths 847, 853 and/or widths 848, 854 may be determined based on at least one of a length (e.g., distance between top and bottom edges 826, 827) or a width (e.g., distance between first and second side edge 833, 834) of the patient transfer device 800. In various embodiments, the length of the patient transfer device 800 may be approximately 89 inches and a width of the patient transfer device 800 may be approximately 47 inches. In various embodiments, a size of the pores within the porous portion 845 may be based on or optimized to accommodate a preferred air flow rate through the air transfer device 800. In some embodiments, the length 847 may be greater than or less than the length 853. In some embodiments, the length 847 is approximately the same as the length 853. In various embodiments, the width 848 may be greater than or less than the width 854. In some embodiments, the width 848 may be approximately the same as the width 854. In various embodiments, a porosity of each of the porous portions 845 and 851 may be uniform throughout each portion. In other embodiments, the porosity of each of the porous portions 845 and 851 may be variable throughout each portion. In some embodiments, a porosity of the porous portion 845 may be approximately greater than, less than, or the same as the porosity of the porous portion 851.

In various embodiments, the patient transfer device 800 may have angled or chamfered edges 840 (similar or equivalent to chamfered edges 740), such as those shown in FIGS. 34 and 35. The chamfered edges 840 may be configured to enable more air pressure to be maintained within the patient transfer device 800 as compared to an amount of air pressure if the patient transfer device 800 was rectangular. In some embodiments, the chamfered edges 840 may have a length and/or height based on or optimized to accommodate a preferred air flow rate and/or air pressure within the air transfer device 800 (i.e., within the chamber formed by the upper and lower layers 805, 810). In some embodiments, the length and/or height of the chamfered edges 840 may be determined based on at least one of a porosity or size of the porous portions 845, 851.

In various embodiments, the patient transfer device 800 includes a plurality of stitch portions 850, as shown in FIGS. 36-38, wherein the upper layer 805 is stitched to the lower layer 810. Such stitch portions 850 may be configured to facilitate air pressure distribution within the patient transfer device 800. In various embodiments, the patient transfer device 800 may include any number of stitch portions 850 (e.g., 4, 6, 12, 19, etc.). In various embodiments, the stitch portions 850 may be disposed in a pattern and/or at distances to facilitate cradling a patient 870 positioned atop the patient transfer device 800, which is disposed on a surface 871 (e.g., bed). As shown in FIG. 36, the stitch portions 850 may cause the patient transfer device 800 to form a cradle surrounding the patient 870 by forming a recessed region 863 disposed between raised regions 860 and 861, wherein the raised regions 860 and 861 support opposite sides of the patient 870. Accordingly, the recessed region 863 and the raised regions 860, 861 may enhance patient comfort and security during sliding of the patient transfer device 800 (i.e., during transfer of the patient 870).

Figures 39, 40:
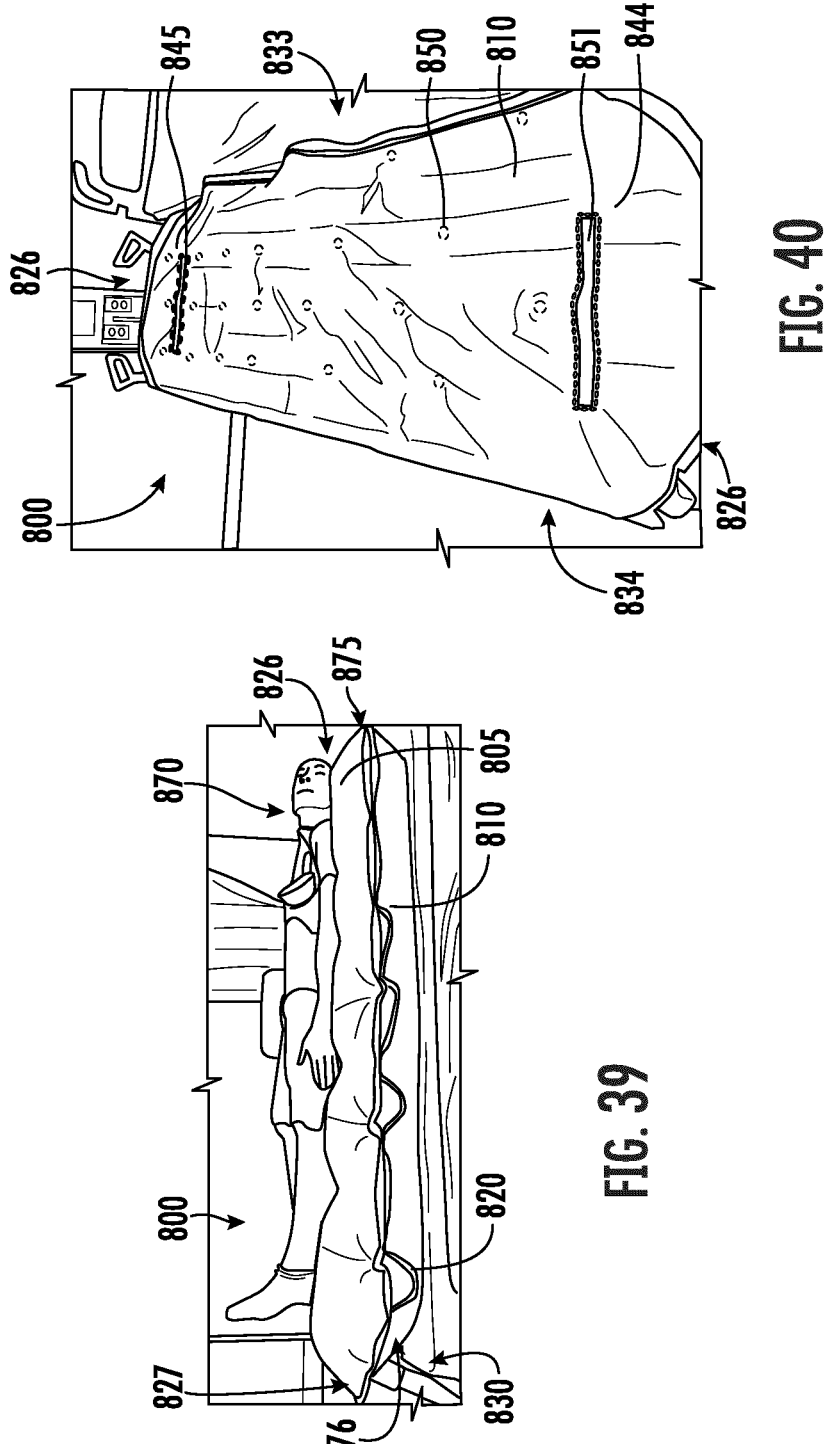
FIG. 39 is a side view of a patient transfer device having multiple porous strips, according to another exemplary embodiment.
FIG. 40 is a bottom view of the patient transfer device of FIG. 39.

In various embodiments, a number or pattern of the stitch portions 850 may be optimized in conjunction with the lengths 847, 853 and/or widths 848, 854 of the porous portions 845, 851. For example, reducing a number of stitch portions 850 near the top edge 826 and increasing the size (e.g., length 847 and/or width 848) of the porous portion 845 may cause an increased air pressure within a head region 875 and form a pillow (as shown in FIG. 37), which may enhance patient comfort. In another embodiment, reducing a number of stitch portions 850 near the bottom edge 827 and increasing the size (e.g., length 853 and/or width 854) of the porous portion 851 may cause an increased air pressure within a foot region 876 and form a foot rest (as shown in FIG. 39), which may enhance circulation and/or comfort of the patient 870. As shown in FIGS. 38 and 40, the porous portions 845 and 851 may be disposed near the top and bottom edges 826 and 827, respectively. In various embodiments, the porous portions 845, 851 may be disposed a distance from each of the top and bottom edges 826, 827 based on an amount of desired friction reduction and/or an intended direction of movement (e.g., via pulling, sliding) of the patient transfer device 800.

As shown in FIGS. 36-40, the patient transfer device 800 may include one or more handles 820 disposed along the outer perimeter of the patient transfer device 800. In various embodiments, the one or more handles 820 may be coupled along the outer perimeter on the lower layer 810 and/or on the upper layer 805. In some embodiments, the patient transfer device 800 may also include one or more straps, which may be coupled along the outer perimeter of the patient transfer device 800 and may extend outwardly therefrom. In various embodiments, the one or more straps may be configured to support, secure, or maintain the patient transfer device 800 upon the support surface.

Figures 41, 42, 43:
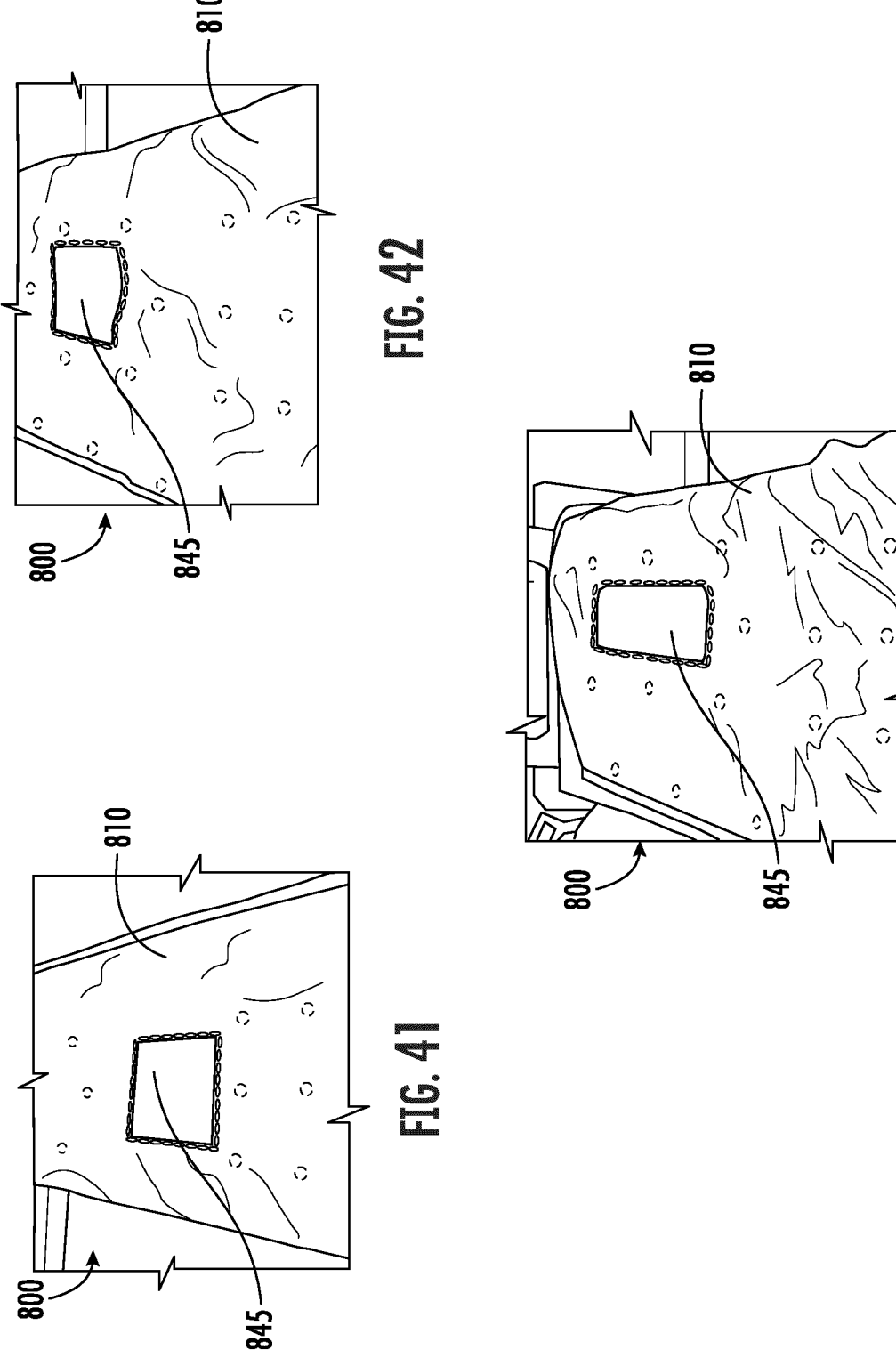
FIGS. 41-47 show bottom views of a patient transfer device having various arrangements and positioning of porous portions having various shapes, according to various exemplary embodiments.

As shown in FIGS. 41-47, the patient transfer device 800 may include one or more porous portions 845, 851 of various shapes, sizes, and/or positions. These porous portion (s) may be disposed in regions configured to support areas bearing greater or concentrated portions of a patient's weight, such as beneath the patient's torso and/or beneath the patient's feet. As shown in FIG. 41, the porous portion 845 may be substantially rectangular or square in shape and disposed on the lower layer 810 in a region configured to be beneath an upper portion or torso of a patient (e.g., the patient 870). In other embodiments, the porous portion 845 may have substantially oval or rounded shape, as shown in FIGS. 42 and 43. In various embodiments, at least one of a position, size, or dimension of the porous portion 845 may be varied or selected based on at least one of a desired use of the patient transfer device 800, a rated weight of the patient transfer device 800, a position of one or more pressure points determined by the patient 870, or a target friction coefficient between the patient transfer device 800 and a surface upon which the patient transfer device 800 engages with.

Figures 44, 45:
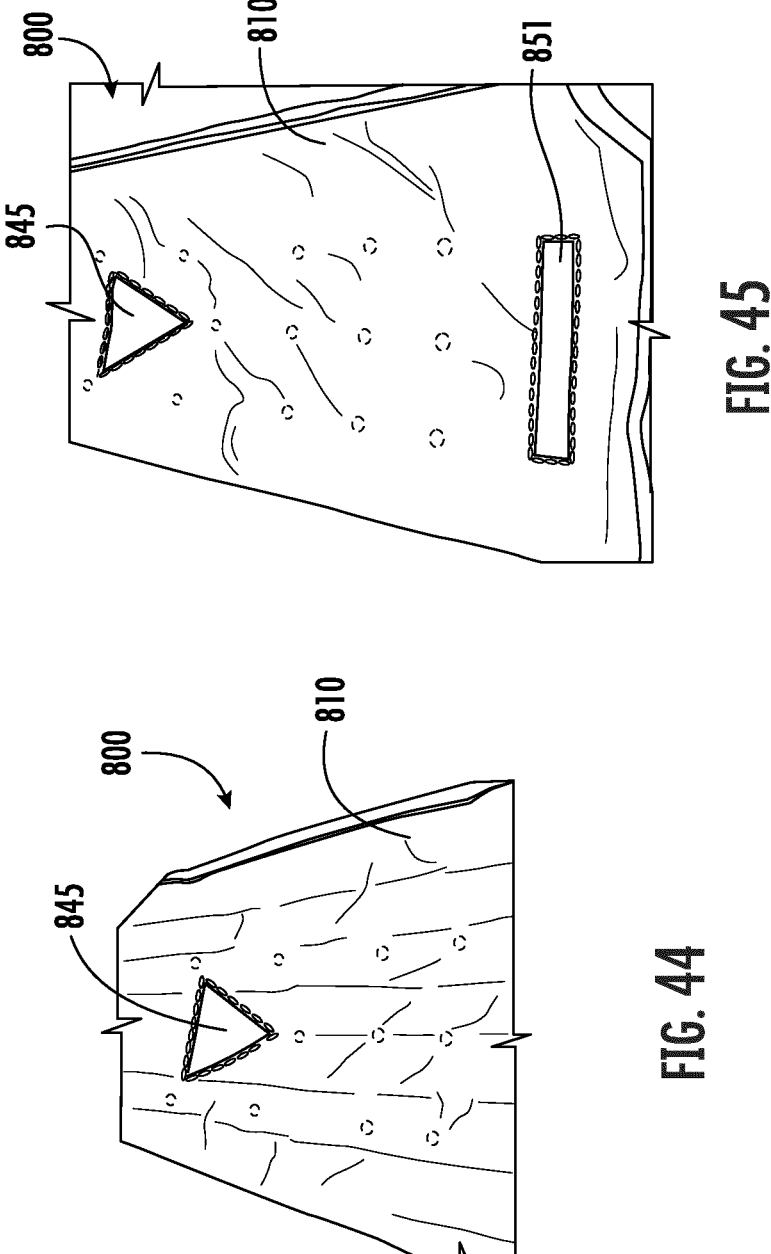

As illustrated in FIG. 44, the porous portion 845 may be substantially triangular in shape and positioned within the lower layer 810 in a region configured to be disposed beneath an upper portion or torso of a patient (e.g., the patient 870). As shown in FIG. 45, the patient transfer device 800 may include two porous portions 845, 851, wherein the porous portion 845 is substantially triangular and configured to be disposed beneath the torso of the patient 870, and wherein the porous portion 851 is configured to be substantially rectangular and disposed to be beneath a lower body region (e.g., feet) of the patient 870.

Figure 47:
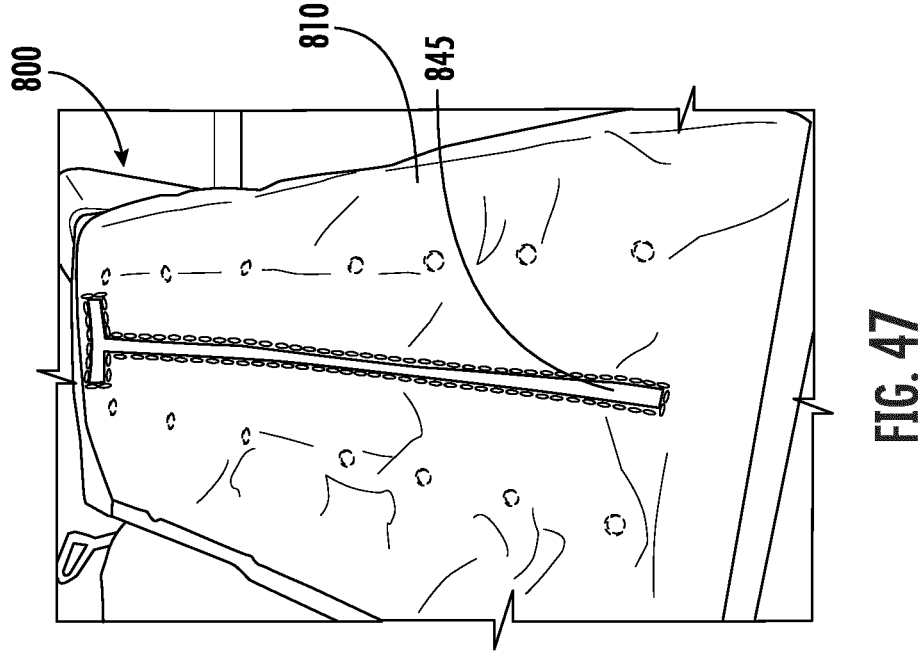
Figure 46:
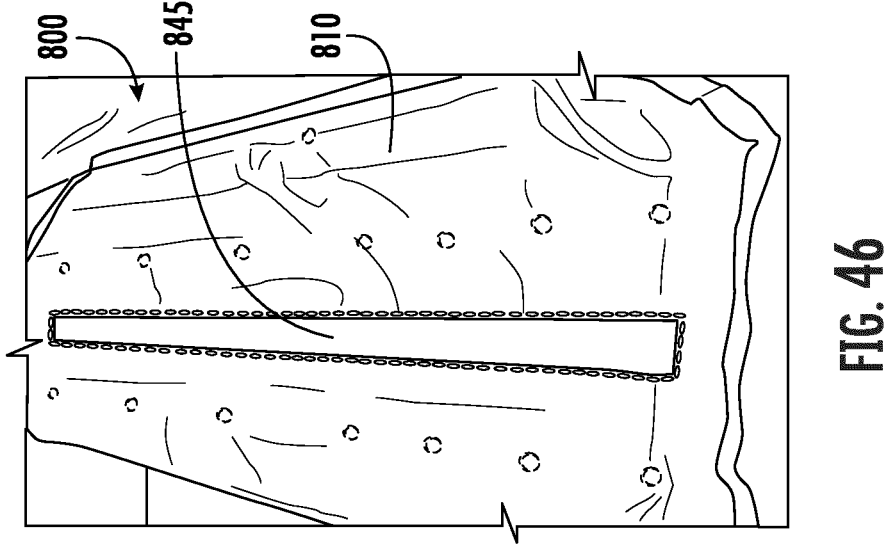

In other embodiments, the patient transfer device 800 may include one or more porous portions 845 configured as longitudinal strips, extending along a length of the patient transfer device 800. As illustrated in FIGS. 46-47, the patient transfer device 800 may be configured such that the porous portion 845 extends along a length of the lower layer 810 of the patient transfer device 800. A width of the porous portion 845 may be varied or selected based on at least one of a desired use of the patient transfer device 800, a rated weight of the patient transfer device 800, or a target friction coefficient between the patient transfer device 800 and a surface upon which the patient transfer device 800 engages with. Although FIGS. 46 and 47 show the porous portion 845 to be substantially rectangular in shape, the porous portion 845 may have fewer or more sides and/or be rounded in shape. In various embodiments, the porous portion 845 may be disposed within a substantially middle region of the lower layer 810 such that a width of the lower layer 810 is substantially bisected by the porous portion 845.

Figures 48, 49:
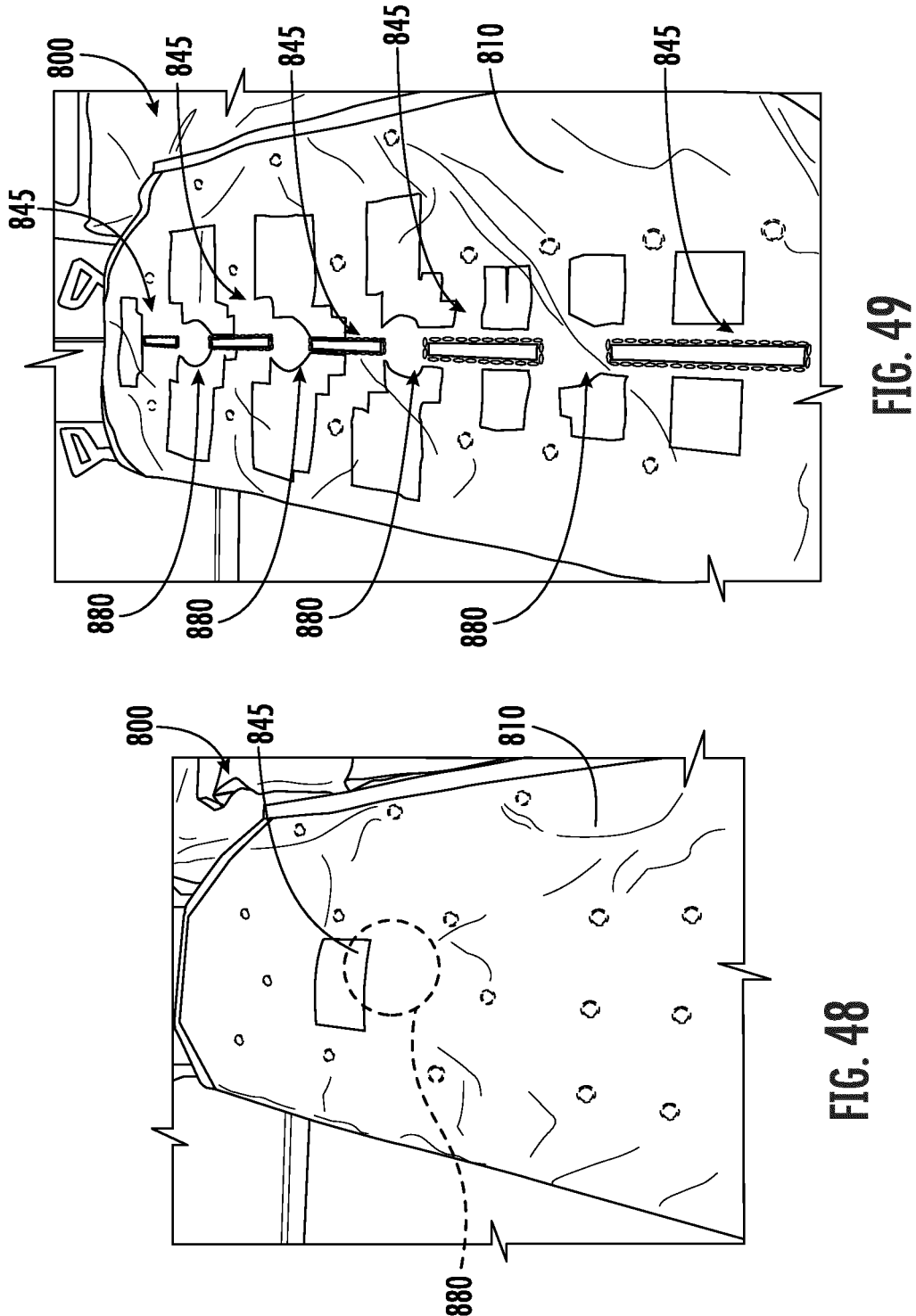
FIGS. 48-49 show bottom views of a patient transfer device having one or more apertures disposed within a bottom layer, according to various exemplary embodiments.

In various embodiments, the lower layer 810 of the patient transfer device 800 may include one or more large apertures 880 positioned at or near pressure points, wherein the one or more apertures 880 are configured to facilitate air flow through the patient transfer device 800 when the patient transfer device 800 is in an inflated state. In various embodiments, the one or more apertures 880 may be configured to have a width or diameter that is approximately 5-15% of the width of the lower layer 810. In various embodiments, the width or diameter of the one or more apertures 880 may be approximately 5 inches. In some embodiments, each of the one or more apertures 880 may have the same width or diameter. In other embodiments, the one or more apertures 880 may have different widths or diameters. As shown in FIG. 48, the patient transfer device 800 may include a single aperture 880 disposed at a pressure point within a region configured to be beneath an upper portion or torso of the patient 870. In other embodiments, the patient transfer device 800 may include multiple apertures 880 disposed within the lower layer 810. As shown in FIG. 49, the patient transfer device 800 may include a plurality of apertures 880 positioned in a linear configuration along a length of the lower layer 810. Although FIG. 49 shows four apertures 880, the patient transfer device 800 may include any number of apertures 880. An addition, the patient transfer device 800 may in some cases include both one or more apertures 880 and one or more porous portions 845. As illustrated in FIG. 49, the patient transfer device 800 may include apertures 880 alternated with porous portions 845, wherein the apertures 880 and the porous portions 845 are arranged in a line extending along a length of the lower layer 810.

Figures 50, 51, 52:
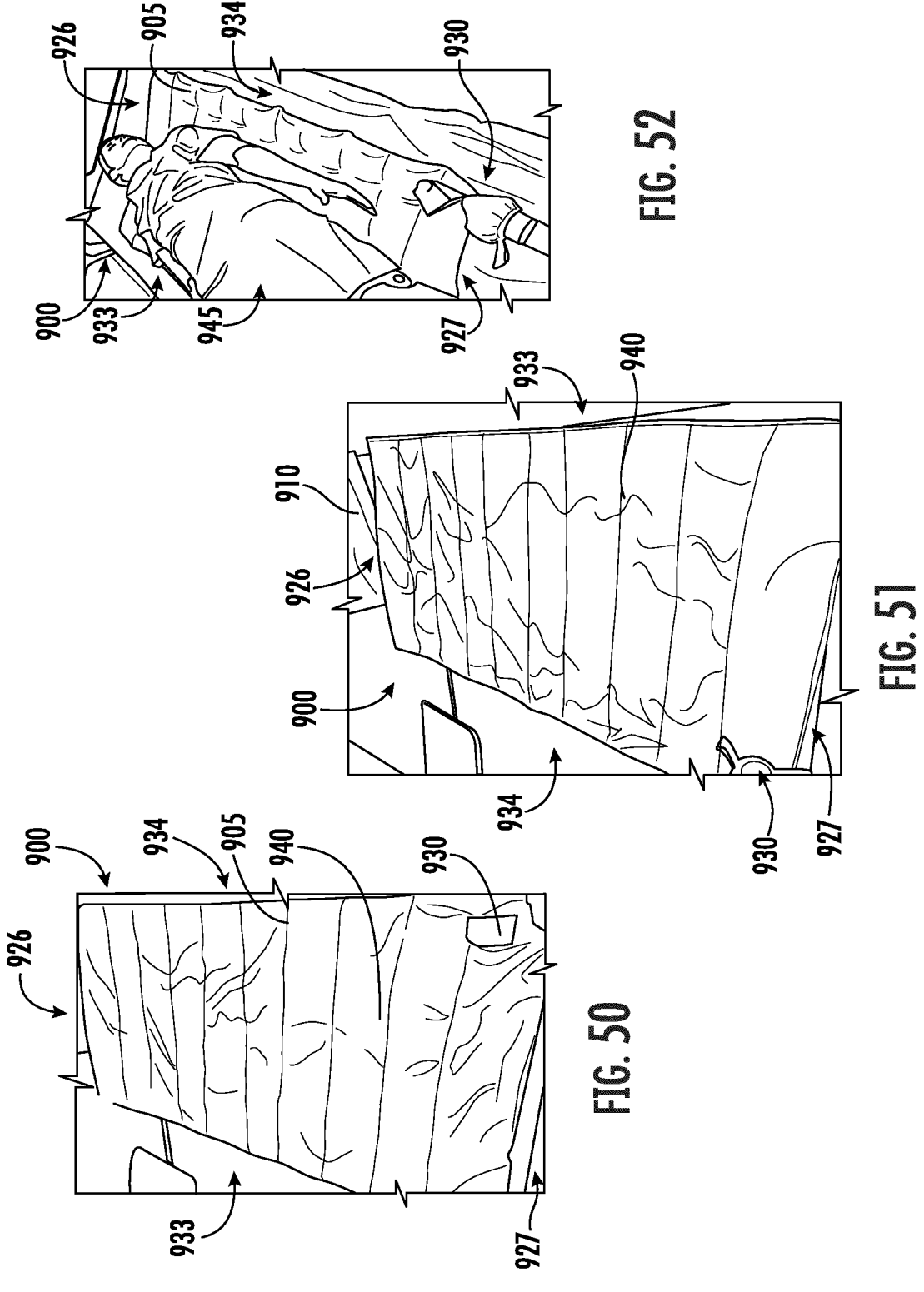
FIG. 50 shows a top view of a patient transfer device having alternating stitch-through portions, according to an exemplary embodiment.
FIG. 51 shows a bottom view of the patient transfer device of FIG. 50.
FIG. 52 shows a perspective view of the patient transfer device of FIG. 50 in an inflated state.

In various embodiments, a patient transfer device may be configured to have a narrow width between stitch-through lines such as, for example, in comparison to a width between stitch-through lines 550 within patient transfer device 500. FIGS. 50-52 show alternate views of a patient transfer device 900, according to an exemplary embodiment. The patient transfer device 900 is configured for facilitating transfer of a patient from a first surface to a second surface. As shown, the patient transfer device 900 includes an upper layer 905 defining an upper surface and a lower layer 910 defining a lower surface. The upper layer 905 and the lower layer 910 are mutually joined along a shared outer perimeter, wherein the outer perimeter forms an outer boundary of the patient transfer device 900 defined between a top edge 926, a bottom edge 927, a first side edge 933, and a second side edge 934. Accordingly, the upper layer 905 and the lower layer 910 form a chamber therebetween. The patient transfer device 900 may also include a port 930 (e.g., quick connect port), which may be configured for connection to one or more airflow devices to enable inflation and deflation of the patient transfer device 900. In various embodiments, the one or more airflow devices may include, but are not limited to, air pumps, vacuums, compressors, etc.

As shown, the patient transfer device 900 includes a plurality of stitch-through lines 940, which are configured to join the upper layer 905 to the lower layer 910. Each of the stitch-through lines 940 are spaced to limit an inflated height of the patient transfer device (measured from a surface supporting the patient transfer device 900 to the upper layer 905), which may increase patient comfort and decrease patient concern during transfer. As illustrated, each of the stitch-through lines 940 extend along a width of the patient transfer device 900. Each of the stitch-through lines 940 are configured to connect to one of the first side edge 933 or second side edge 934 such that none of the stitch-through lines 940 connect to both of the side edges 933, 934. Furthermore, the stitch-through lines 940 are configured to alternate such that adjacent stitch-through lines 940 do not connect to the same side edge (i.e., two adjacent stitch-through lines 940 would not both connect to either the first side edge 933 or the second side edge 934). Each stitch-through line 940 is configured such that a terminal end of the stitch-through line 940 is spaced from an edge of the patient transfer device 900 opposite an edge to which the stitch-through line 940 is connected. Accordingly, the stitch-through lines 940 create a non-linear air flow path through the patient transfer device 900, wherein air flows between adjacent stitch-through line 940 and at terminal ends of each of the stitch-through lines 940 (i.e., the air "snakes" through the patient transfer device 900). In this manner, when the patient transfer device 900 is supplied with air (e.g., via the port 930), the patient transfer device 900 inflates beginning at the end nearest the port 930 (e.g., near the bottom edge 927) and sequentially inflates channels defined between adjacent stitch-through lines 940 until air reaches an opposing end of the patient transfer device furthest from the port 930 (e.g., near the top edge 926). Accordingly, when the patient transfer device 900 is fully inflated, as illustrated in FIG. 52, a patient 945 may be lifted a distance from the surface supporting the patient transfer device 900. In various embodiments, a distance between adjacent stitch-through lines may be approximately 5 inches. In various embodiments, each stitch-through line 940 may be configured such that a terminal end of the stitch-through line 940 is spaced approximately 2-5 inches from either edge of the patient transfer device 900 opposite an edge to which the stitch-through line 940 is connected.

Figure 53:
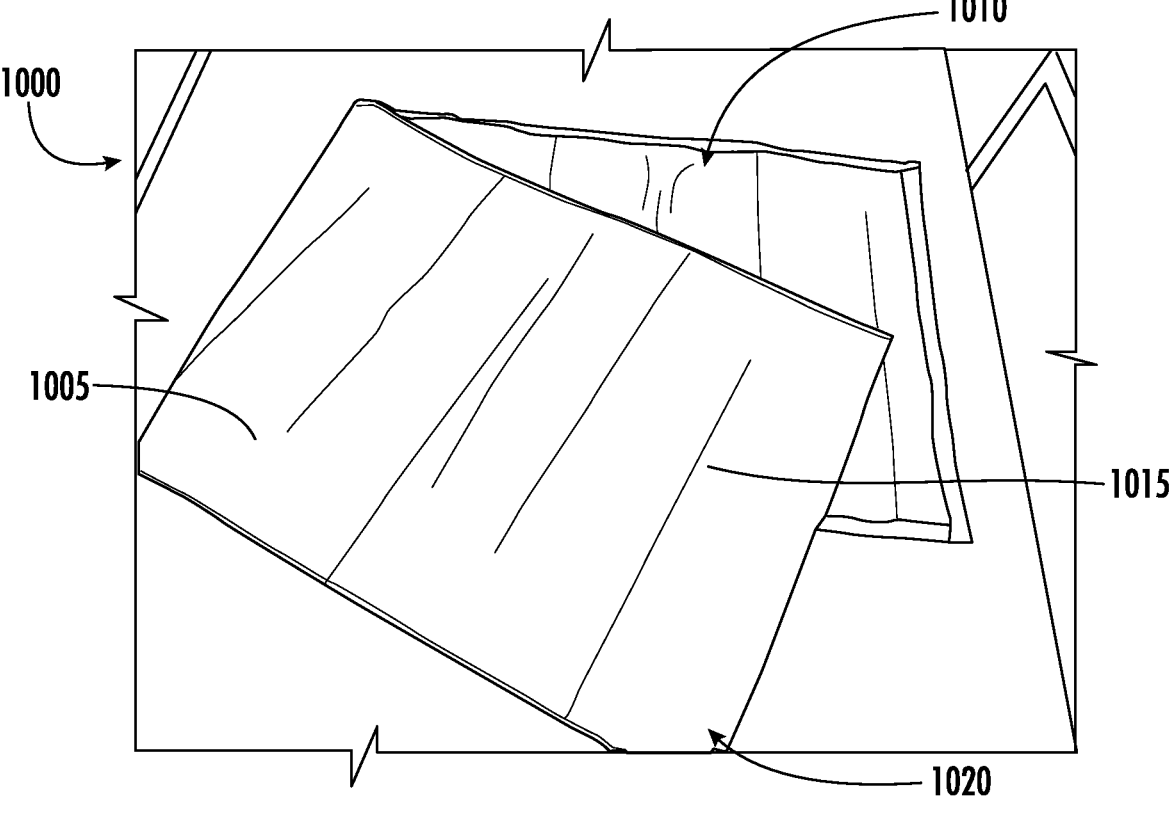
FIG. 53 shows a top perspective view of a patient transfer device, according to an exemplary embodiment.

In various embodiments, a patient transfer device may be configured to slide relative to itself while inflated. FIG. 53 shows a top perspective view of a patient transfer device 1000, according to an exemplary embodiment. The patient transfer device 1000 is configured for facilitating transfer of a patient from a first support surface to a second support surface. As shown, the patient transfer device 1000 includes a first layer 1005 defining a first device surface and a second layer 1010 defining a second device surface. The first layer 1005 and the second layer 1010 are mutually joined along a shared outer perimeter, wherein the outer perimeter forms an outer boundary of the patient transfer device 1000. Accordingly, the first layer 1005 and the second layer 1010 form a chamber therebetween. The patient transfer device 1000 may also include a port 1020 (e.g., quick connect port), which may be configured for connection to one or more airflow devices to enable inflation and deflation of the patient transfer device 1000. In various embodiments, the one or more airflow devices may include, but are not limited to, air pumps, vacuums, compressors, etc.

The patient transfer device 1000 is configured fold in a direction substantially perpendicular to a longest dimension of the patient transfer device 1000 such that the first layer 1005 is configured to contact the surface on which the patient transfer device 1000 is disposed (e.g., the first support surface or the second support surface) and configured to contact and support the patient. Similarly, the second layer 1010 is configured to be in contact with itself. Accordingly, a first terminal end of the patient transfer device 1000 is configured to be adjacent the surface on which the patient transfer device 1000 is disposed (e.g., the first support surface or the second support surface) and a second terminal end of the patient transfer device 1000 is separated or disposed a distance from the surface on which the patient transfer device 1000 is disposed. The first layer 1005 may have a first friction coefficient and the second layer 1010 may have a second friction coefficient, wherein the second friction coefficient is less than the first friction coefficient such that the second layer 1010 is configured to slide as it engages with itself in response to a force applied to the second terminal end of the patient transfer device 1000. The second layer 1010 may be configured as a porous layer, such that air flowing with the patient transfer device 1000 is configured to pass through the second layer 1010. Accordingly, when the patient transfer device 1000 is inflated in a folded state, an air pocket forms between the terminal ends of the folded patient transfer device 1000 such that a coefficient of friction between engaging portions of the second layer 1010 is reduced to facilitate sliding therebetween.

During use, the patient transfer device 1000 may be folded and placed beneath a patient such that the first layer 1005 is in contact with the support surface (e.g., the first support surface or the second support surface) and with the patient. The patient transfer device 1000 may then be inflated by providing an airflow at the port 1020. A pulling force may then be applied to the second terminal end of the patient transfer device (i.e., the terminal end not adjacent the support surface) such that the second layer 1010 engages and slides relative to itself to facilitate transfer of the patient.

Figures 54, 55:
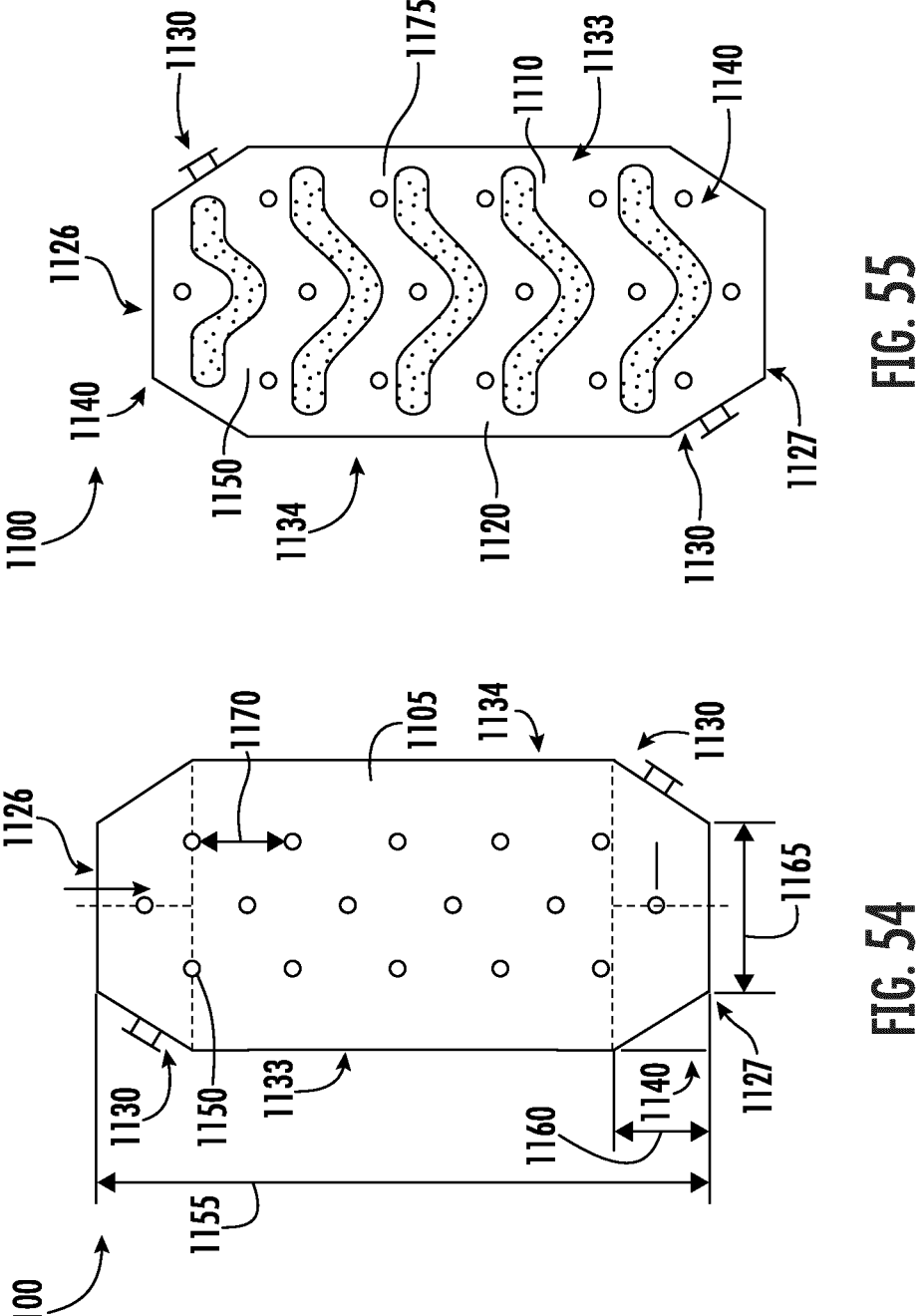
FIG. 54 shows a schematic representation of a top view of a symmetric patient transfer device, according to an exemplary embodiment.
FIG. 55 shows a schematic representation of a bottom view of the patient transfer device of FIG. 54.

In various embodiments, a patient transfer device may be configured to be symmetric such that ends of the patient transfer device may support either of a patient's upper or lower body. FIGS. 54 and 55 show top and bottom views of a patient transfer device 1100, according to an exemplary embodiment. The patient transfer device 1100 is configured for facilitating transfer of a patient from a first surface to a second surface. As shown, the patient transfer device 1100 includes an upper layer 1105 defining an upper surface and a lower layer 1110 defining a lower surface configured to be in contact with the first surface or second surface. The upper layer 1105 and the lower layer 1110 are mutually joined along a shared outer perimeter, wherein the outer perimeter forms an outer boundary of the patient transfer device 1100 defined between a top edge 1126, a bottom edge 1127, a first side edge 1133, and a second side edge 1134. Accordingly, the upper layer 1105 and the lower layer 1110 form a chamber therebetween. The patient transfer device 1100 may also include a port 1130 (e.g., quick connect port), which may be configured for connection to one or more airflow devices to enable inflation and deflation of the patient transfer device 1100. In various embodiments, the one or more airflow devices may include, but are not limited to, air pumps, vacuums, compressors, etc.

As shown in FIGS. 54 and 55, the patient transfer device 1100 is symmetric such that the top edge 1126 and the bottom edge 1127 are configured to be substantially identical in both form and function. Similarly, the first side edge 1133 and the second side edge 1134 are configured to be substantially identical in both form and function. Accordingly, use of the patient transfer device 1100 is not limited based on an orientation of the edges 1126, 1127 or the side edges 1133, 1134 so long as the lower layer 1110 is disposed to contact the surface on which the patient transfer device is positioned (e.g., the first surface or the second surface). As shown, the patient transfer device 1100 includes two ports 1130, wherein a first of the two ports 1130 is disposed near the top edge 1126 and the second of the two ports 1130 is disposed near the bottom end 1127. Positioning of a port 1130 near each of the edges 1126, 1127 of the patient transfer device 1100 enables case of access to a port 1130 regardless of orientation of the patient transfer device 1100. As shown, the patient transfer device 1100 includes chamfered edges 1140 disposed between the top edge 1126 and the side edges 1133, 1134 and between the bottom edge 1127 and the side edges 1133, 1134. The chamfered edges 1140 may increase an air pressure within the patient transfer device 1100. In various embodiments, at least one of a width or height 1160 of the chamfered edges 1140 may be approximately 12 inches. In various embodiments, the top edge 1126 and the bottom edge 1127 may each have a length 1165 of approximately 20 inches. In some embodiments, the patient transfer device 1100 may have a length 1155 of approximately 89 inches, wherein the length 1155 corresponds to the perpendicular distance between the top edge 1126 and the bottom edge 1127.

As illustrated, the patient transfer device 1100 includes a plurality of stitch-through portions 1150, wherein the upper layer 1105 and the lower layer 1110 are connected. Each of the stitch-through portions 1150 are configured to increase pressure within the patient transfer device 1100 when the patient transfer device 1100 is inflated (e.g., via at least one of the ports 1130). In various embodiments, the stitch-through portions 1150 may be arranged in columns in a staggered configuration as shown in FIGS. 54 and 55. In some embodiments, a perpendicular distance between the side edges 1133, 1134 and an adjacent column of stitch-through portions 1150 is approximately 12 inches. In some embodiments, perpendicular distance between the edges 1126, 1127 and an adjacent column of stitch-through portions 1150 is approximately 6 inches. In various embodiments, a distance 1170 between adjacent stitch-through portions 1150 within each column of stitch-through portions 1150 may be approximately 6 inches.

As illustrated in FIG. 55, the patient transfer device 1100 may include a plurality of porous portions 1175 disposed within the lower layer 1110. Each of the porous portions 1175 may be configured to have a width corresponding to a width between outermost columns of stitch-through portions 1150. In various embodiments, each of the porous portions 1175 may be disposed within the lower layer 1110 such that each porous portion 1175 curves around stitch-through portions 1150. Each of the porous portions 1175 is configured to enable airflow therethrough when the patient transfer device 1100 is inflated. Airflow through each of the porous portions 1175 consequently creates an air pocket between the lower layer 1110 and the support surface upon which the patient transfer device 1100 is positioned. Accordingly, when the patient transfer device 1100 is inflated and air flows through each of the porous portions 1175, a coefficient of friction between the lower layer 1110 and the support surface is decreased. During use, the patient transfer device 1100 may be inflated by providing airflow through at least one of the ports 1130. Once inflated, the lower layer 1110 of the patient transfer device 1100 may slide relative to the support surface in response to an applied pull force (i.e., by medical personnel). In various embodiments, the patient transfer device 1100 includes one or more straps, loops, and/or handles disposed within an outer region 1120 adjacent each of the outer side edges 1133, 1134.

Figure 56:
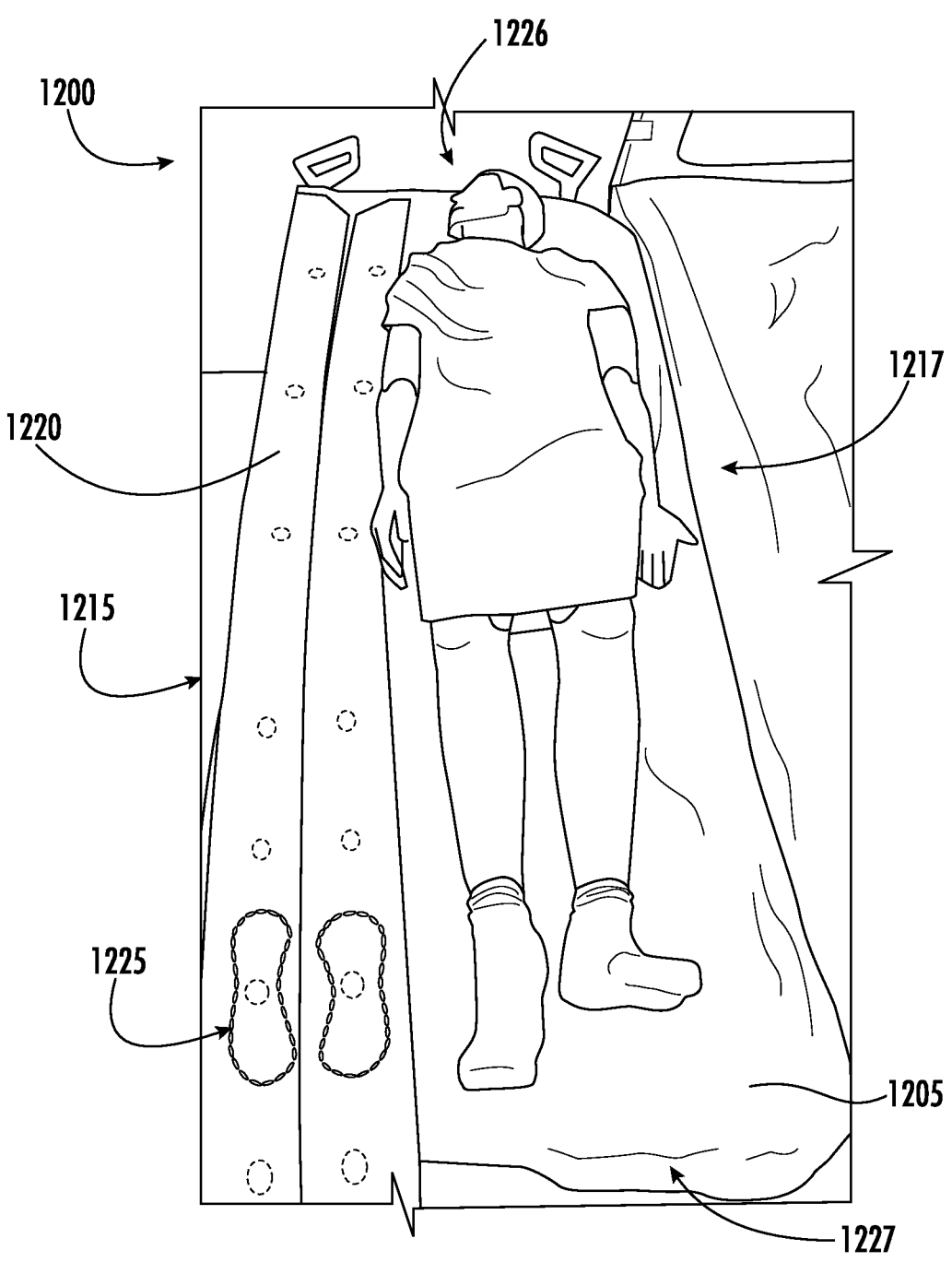
FIG. 56 shows a top perspective view of a patient transfer device having indicia to indicate orientation of the device, according to an exemplary embodiment.

In various embodiments, a patient transfer device may include one or more labels and/or indicators to indicate an orientation. Such labels and/or indicators may alert medical professionals or personnel how to position the patient transfer device to facilitate patient transfer. FIG. 56 shows a top perspective view of a patient transfer device 1200 (e.g., similar or equivalent to patient transfer devices 100, 200, 300, 400, 500, 600, 700, 800, 900, 1000), according to an exemplary embodiment. As shown, the patient transfer device 1200 is configured to transfer a patient disposed on an upper layer 1205. The patient transfer device 1200 is defined between a first side edge 1215, a second side edge 1217, top edge 1226, and a bottom edge 1227. In various embodiments, the patient transfer device 1200 is configured to support a patient's head near the top edge 1126 and a patient's feet near the bottom edge 1227. The patient transfer device 1200 accordingly may include various features and/or contours specific to support various patient regions including, but not limited to, the patient's head and feet. Accordingly, the patient transfer device 1200 includes an indicator region 1220 disposed near at least one of the first side edge 1215 or the second side edge 1217. The indicator region 1220 includes one or more indicia 1225, which specify a particular use orientation of the patient transfer device 1200. For example, the one or more indicia 1225 may include a depiction of feet near the bottom edge 1227 to indicate that the patient transfer device 1220 should be oriented such that a region near the bottom edge 1227 is positioned to support the patient's feet. In other embodiments, the one or more indicia may include various textual labels, arrows, colors, or other visual indicators to specify a use orientation of the patient transfer device 1200. In various embodiments, the one or more indicia may include various tactile indicators (e.g., bumps, ridges, etc.) in addition to or as an alternative to visual indicators.

Figures 57, 58, 59, 60, 61:
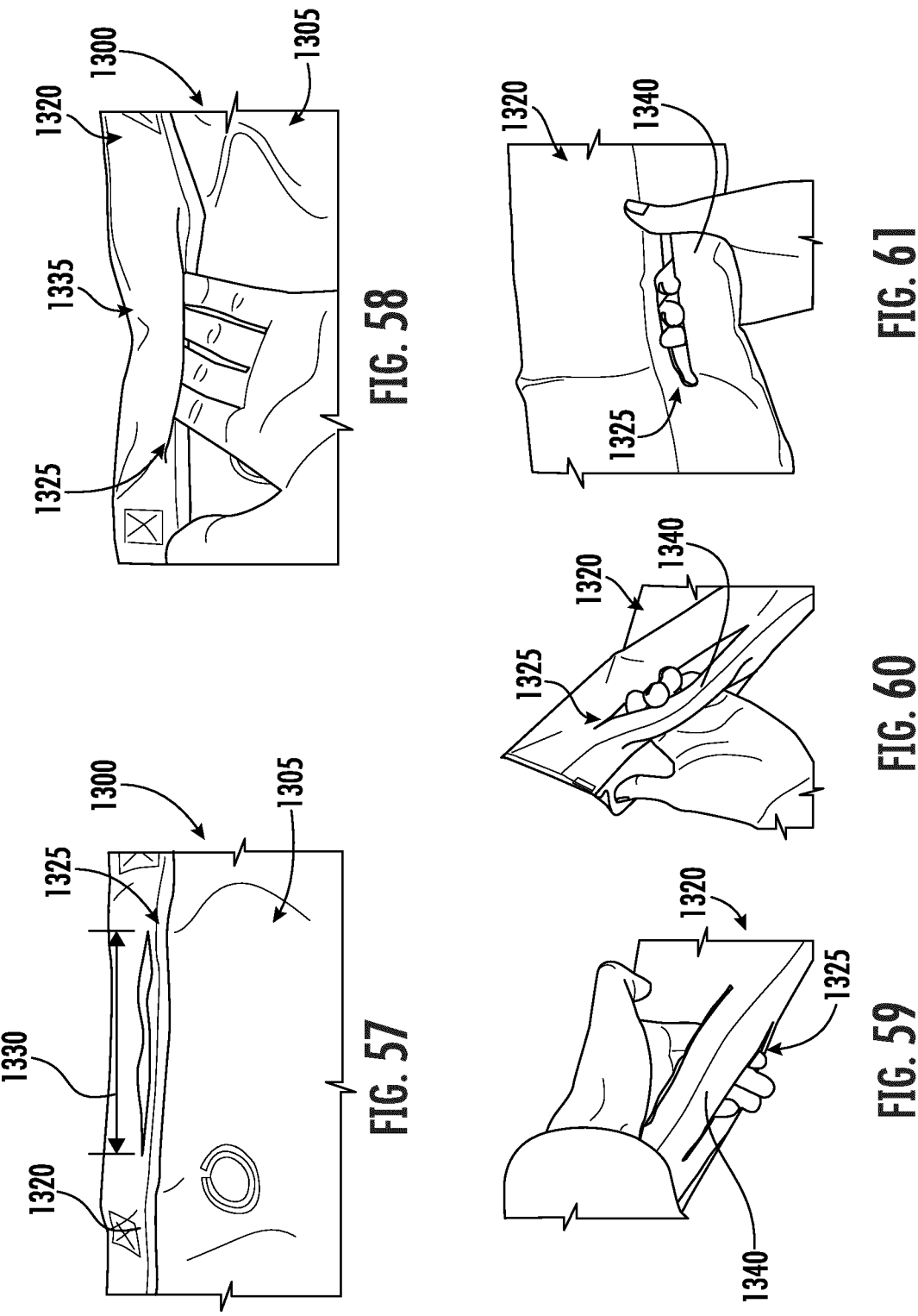
FIGS. 57-58 show alternate top views of a pocket handle disposed within a patient transfer device, according to an exemplary embodiment.
FIGS. 59-61 show alternate views of an embedded handle disposed within a patient transfer device, according to an exemplary embodiment.

A patient transfer device may include various mechanisms to facilitate grasping, pulling, pushing, or otherwise handling of the patient transfer device. FIGS. 57-61 show alternate views of pocket handles 1325 disposed within a fold 1320 formed at an outer edge of a patient transfer device 1300 (e.g., similar or equivalent to patient transfer devices 100, 200, 300, 400, 500, 600, 700, 800, 900, 1000, 1100, 1200), according to an exemplary embodiment. As shown, the patient transfer device 1300 includes one or more handles 1325 disposed within a fold 1320 formed at an edge of an upper layer 1305, which is configured to support a patient. As shown in FIGS. 57 and 58, the handles 1325 may be slits disposed within the fold 1320, which enable a user (e.g., medical personnel) to insert their into hands/fingers into the fold 1320 and facilitate grasping the patient transfer device 1300. In various embodiments, the slits of the one or more handles 1325 has a width 1330 and may be disposed on a same side of the fold 1320 as a top surface of the upper layer 1305. In other embodiments, the slits of the one or more handles 1325 may be disposed on a side of the fold 1320 opposite the top surface of the upper layer 1305. In various embodiments, each of the handles 1325 may have a depth ranging from approximately 1 inch to approximately 3 inches.

In other embodiments, each of the handles 1325 may be embedded within the fold 1320, wherein each handle 1325 is formed between two openings on a same side of the fold 1320, as shown in FIGS. 59 and 60. As illustrated, a user (e.g., medical personnel) may grasp a portion 1340 of the fold 1320 to facilitate grasping, pulling, or handling of the patient transfer device 1300. In yet other embodiments, each of the handles 1325 may be formed between two openings on opposite sides of the fold 1320, as shown in FIG. 61. As illustrated, the user may grasp the portion 1340, which is disposed along an outermost edge of the fold 1320. In various embodiments, the openings may be slits, cuts, shaped openings (e.g., oval-shaped), or other formed apertures disposed within or through the fold 1320. In various embodiments, the one or more handles 1325 may be disposed within particular regions along the outer edges of the patient transfer device 1300. In other embodiments, the one or more handles 1325 may be disposed along an entire outer edge of the patient transfer device 1300. In various embodiments, each of the handles 1325 may be formed on a same side of the fold 1320. In various embodiments, the handles 1325 may be alternately formed on opposing sides of the fold 1320.

Figure 63:
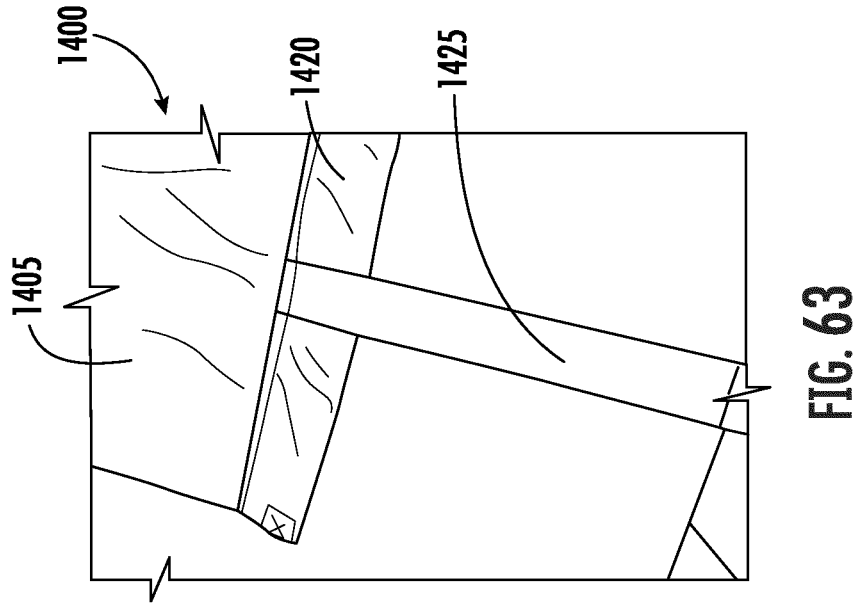
FIGS. 62 and 63 show alternate top views of a handle coupled to an outer edge of a patient transfer device, according to various exemplary embodiments.
Figure 62:
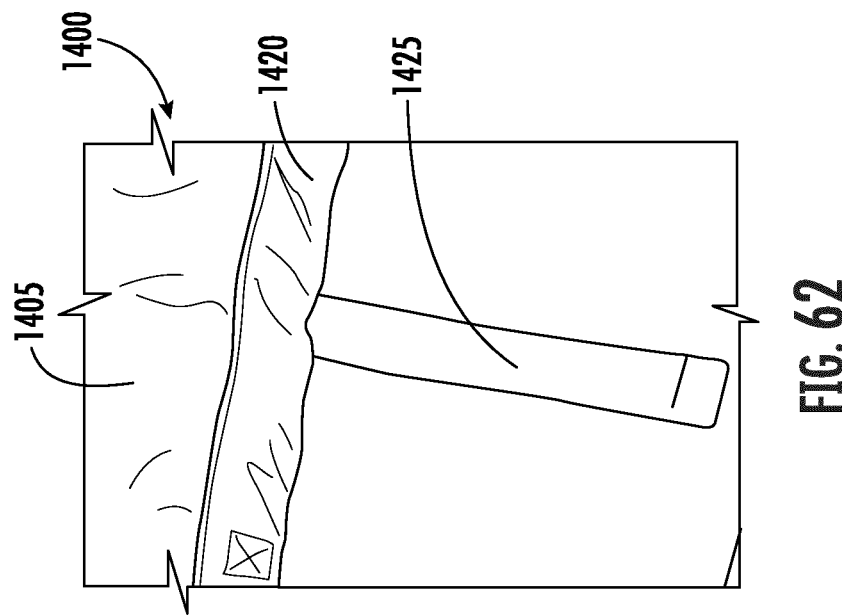

In various embodiments, a patient transfer device may include one or more handles disposed along an outer edge of the device. FIGS. 62 and 63 show alternate views of handles 1425, which are coupled to an outer edge 1420 of a patient transfer device 1400 (e.g., similar or equivalent to patient transfer devices 100, 200, 300, 400, 500, 600, 700, 800, 900, 1000, 1100, 1200, 1300), according to an exemplary embodiment. As shown in FIG. 62, the patient transfer device 1400 includes a rope-type handle 1425 coupled to the outer edge 1420 of the patient transfer device 1400. A length of the handle 1425 may facilitate grasping, pulling, or handling by a user (e.g., medical professional). The one or more handles 1425 may be woven and may include a loop, knob, or other feature at a terminal end of each handle 1425 to facilitate grasping, holding, pulling, or handling by the user. As shown in FIG. 62, the one or more handles 1425 may be coupled to the outer edge 1420 on a side of the patient transfer device 1400 opposite a top surface of the upper layer 1405. In other embodiments, as shown in FIG. 63, the one or more handles 1425 may be coupled to the outer edge 1420 on a same side of the patient transfer device 1400 as the top surface of the upper layer 1405.

Figure 65:
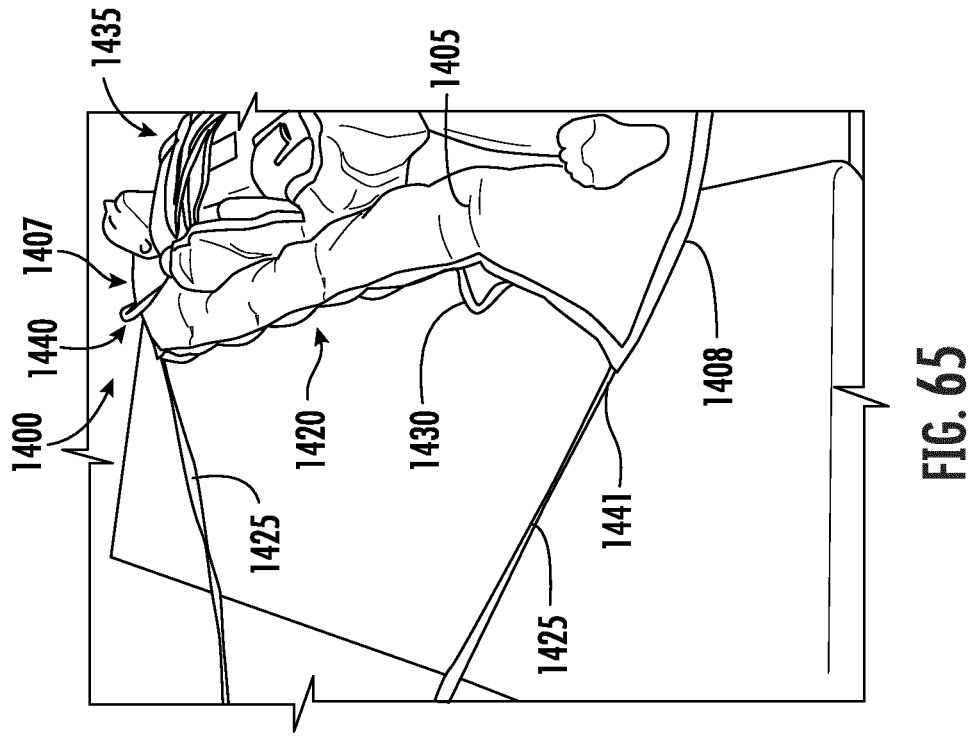
FIG. 65 shows another perspective view of the patient transfer device of FIG. 64.
Figure 64:
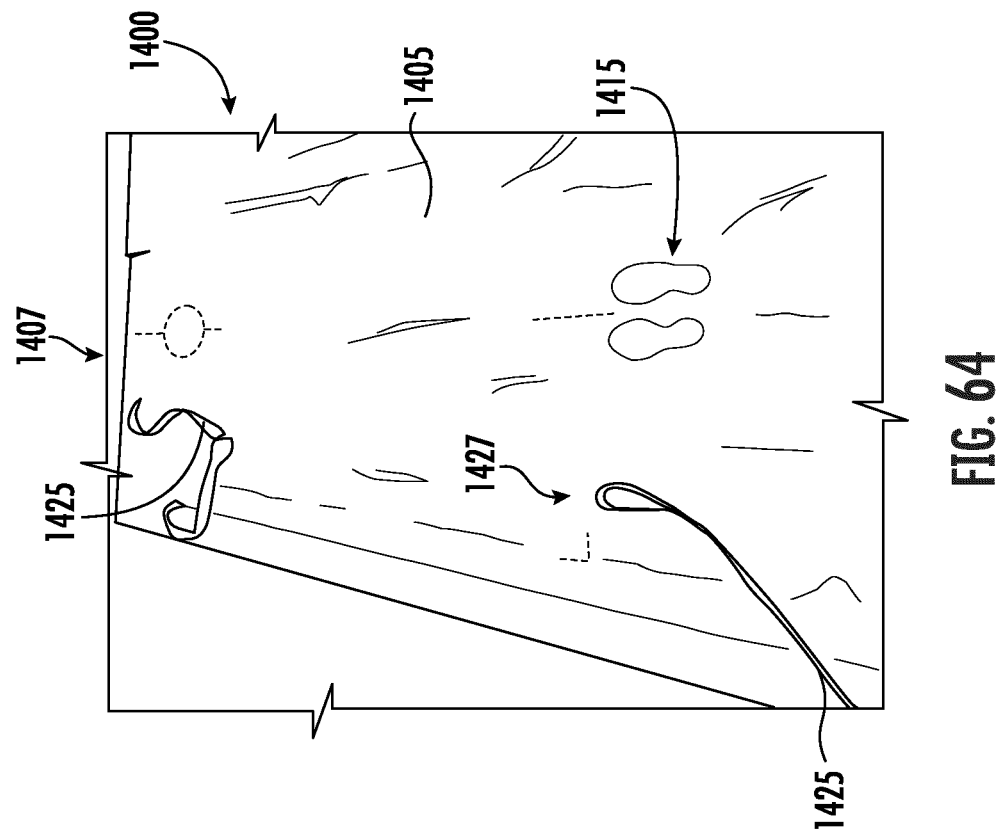
FIG. 64 shows a top perspective view of a patient transfer device having extended handles, according to an exemplary embodiment.

FIGS. 64 and 65 show top and top perspective views, respectively, of the patient transfer device 1400, according to an exemplary embodiment. As shown, the one or more handles 1425 may be coupled to the patient transfer device 1400 along the outer edge 1420 in regions near a top end 1407 and a bottom end 1408 at connection points 1440 and 1441, respectively. A first end of each of the handles 1425 is coupled to the outer edge 1420 of the patient transfer device 1400 at a location that is approximately halfway between the top and bottom ends 1407, 1408. A length of each of the handles 1425 between the first end and the terminal end 1427 is contained within one or more seams disposed along and parallel to the outer edge 1420, wherein the one or more seams containing the handles 1425 terminate in an opening at or near the top and bottom ends 1407, 1408 of the patient transfer device 1400. Accordingly, the terminal ends 1427 of the handles 1425 extend outward from the outer edge 1420 at or near the top and bottom ends 1407, 1408 and are configured to be held, grasped, or otherwise anchored to facilitate pulling of the patient transfer device 1400. Accordingly, the handles 1425 may enable a user (e.g., medical personnel) to pull or otherwise move the patient transfer device 1400 without needing to reach over the device while transferring a patient and case the pull force required. In various embodiments, the patient transfer device 1400 may further include one or more secondary handles 1330 disposed along a length of the outer edge 1420.

Figures 66, 67, 68:
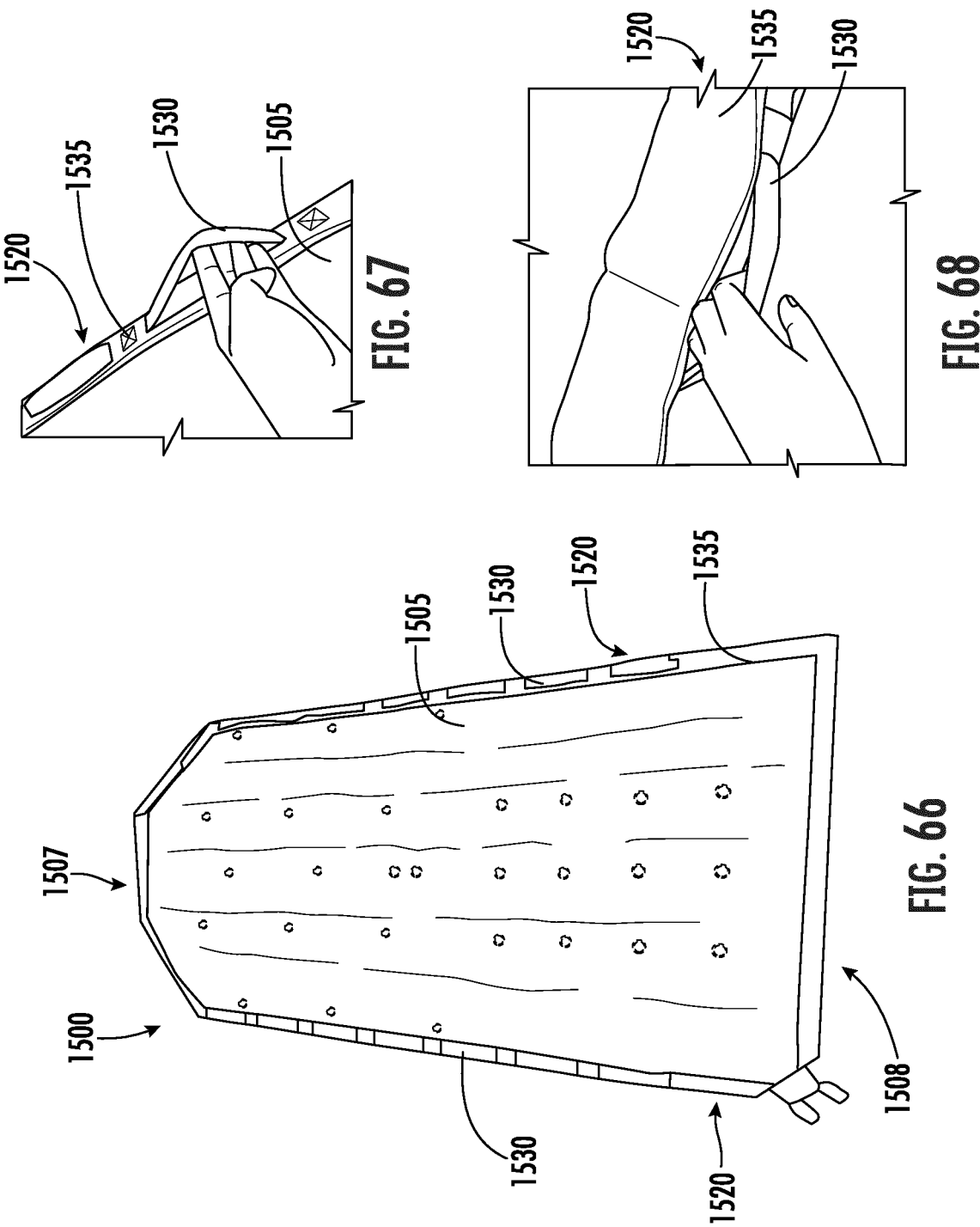
FIG. 66 shows a top perspective view of a patient transfer device having interlaced handles, according to an exemplary embodiment.
FIGS. 67 and 68 show alternate views of a handle of the patient transfer device of FIG. 66.

In various embodiments, a patient transfer device may include one or more handles that are interlaced within an outer edge of the patient transfer device. FIGS. 66-68 show alternate views of a patient transfer device 1500 (e.g., similar or equivalent to patient transfer devices 100, 200, 300, 400, 500, 600, 700, 800, 900, 1000, 1100, 1200, 1300, 1400), according to an exemplary embodiment. The patient transfer device 1500 includes an upper layer 1505 coupled to an opposing lower layer about a shared outer perimeter forming a chamber therein. The patient transfer device 1500 may include one or more ports (e.g., quick connect ports), which are configured to facilitate connection to one or more devices to provide air for inflating the patient transfer device 1500. The patient transfer device 1500 includes a top edge 1507 and a bottom edge 1508. The patient transfer device 1500 further includes two substantially parallel outer edges 1520, which are disposed substantially perpendicular to each of the top edge 1507 and the bottom edge 1508. As shown, the patient transfer device 1500 includes a plurality of handles 1530, which are disposed within the outer edge 1520 and facilitate grasping, holding, pulling, or otherwise handling of the patient transfer device 1500. The handles 1530 along an edge 1520 are formed from a singular section, which is coupled to the patient transfer device at opposite terminal ends near each of the top edge 1507 and the bottom edge 1508. As shown in FIGS. 67 and 68, each of the handles 1530 may be pulled away from the outer edge 1520, causing tension in each of the remaining handles 1530. The handles 1530 may be defined between anchor points 1535, which are formed within the outer edge 1520. During use, a user (e.g., medical personnel) may grasp a handle 1530 from the plurality of handles 1530 disposed along an outer edge 1520 of the patient transfer device 1500, wherein the grasped handle 1530 elongates and causes tension along the entirety of the outer edge 1520. Accordingly, the generated tension facilitates case of pulling or movement of the patient transfer device 1500 by the user.

In other embodiments, a patient transfer device may include one or more adjustable handles. FIGS. 69 and 70 show a patient transfer device 1600 (similar or equivalent to any one of the preceding patient transfer devices 100-1500) having one or more adjustable handles, according to an exemplary embodiment. The patient transfer device 1600 includes an upper layer 1505 coupled to an opposing lower layer about a shared outer perimeter forming a chamber therein. The patient transfer device 1600 may include one or more ports (e.g., quick connect ports), which are configured to facilitate connection to one or more devices to provide air for inflating the patient transfer device 1600. The patient transfer device 1600 includes a top edge 1607 and a bottom edge 1608. The patient transfer device 1600 further includes two substantially parallel outer edges 1620, which are disposed substantially perpendicular to each of the top edge 1607 and the bottom edge 1608. The patient transfer device 1600 further includes one or more handles 1625 disposed near at least one of the outer edges 1620. Each of the handles 1625 may include a loop and may be configured to be anchored to a longitudinal line 1630, which extends substantially parallel to at least one of the outer edges 1620. Each of the handles 1625 may be configured to articulate with the line 1630 such that each handle 1625 may be longitudinally adjusted along the outer edge 1620 of the patient transfer device 1600. In various embodiments, the longitudinal line may be defined between a first end 1633 and a second end 1635, defining an adjustable range for the handle 1625 coupled thereto. In various embodiments, the patient transfer device 1600 may include a singular longitudinal line 1630 disposed along the outer edges 1620. In other embodiments, the patient transfer device 1600 may include multiple longitudinal lines 1630 corresponding to multiple handles 1625 disposed along the outer edges 1620. In some embodiments, the longitudinal line 1630 may be configured as a cord configured to articulate within an inner bore or aperture disposed within each of the handles 1625. In other embodiments, the longitudinal line 1630 may be configured to have one or more protruding features (e.g., serrated features), which may articulate or engage with one or more complementary features of the one or more handles 1625. During use, a user (e.g., medical personnel) may grasp one or more of the handles 1625 disposed along at least one of the outer edges 1620 of the patient transfer device 1600, adjust the one or more handles 1625 to be positioned along the outer edge 1620 in a preferred position, and pull on the one or more handles 1625 to facilitate moving the patient transfer device 1600.

In yet other embodiments, a patient transfer device may include removable straps. FIG. 71 shows a top view of a patient transfer device 1700, according to an exemplary embodiment. The patient transfer device 1700 may be similar or equivalent to any of the patient transfer devices 100-1500. As shown, the patient transfer device 1700 includes a upper layer 1705 configured to support a patient thereon, and an opposing lower layer configured to be in contact with a surface on which the patient transfer device 1700 is disposed. The patient transfer device 1700 is configured to support a patient positioned between a top end 1707 and a bottom end 1708. As shown, the patient transfer device 1700 may include a plurality of apertures 1710 disposed along an outer edge 1720, wherein the outer edge 1720 is substantially perpendicular to each of the top end 1707 and the bottom end 1708. The patient transfer device 1700 includes at least one strap 1725, which is configured to connect to the apertures 1710 at terminal ends 1727 and 1728. Each of the terminal ends 1727 and 1728 may include one or more clips or hooks, which facilitate coupling of the strap 1725 to apertures 1710. Accordingly, a user (e.g., medical personnel) may selectively couple at least one strap 1725 to the outer edge 1720 of the patient transfer device 1700 by connecting terminal ends 1727 and 1728 of the strap 1725 to apertures 1710 corresponding to a desired position of the strap 1725. The strap 1725 may be subsequently removed and repositioned as necessary by coupling and uncoupling the terminal ends 1727 and 1728 from the apertures 1710. Furthermore, adjustable positioning of the terminal ends 1727 and 1728 may allow the user to change a length of the strap 1725 such that the strap 1725 may be grasped or may be hooked on the user's shoulders (or other portion of the upper body) to facilitate pulling or movement of the patient transfer device 1700.

Figure 73:
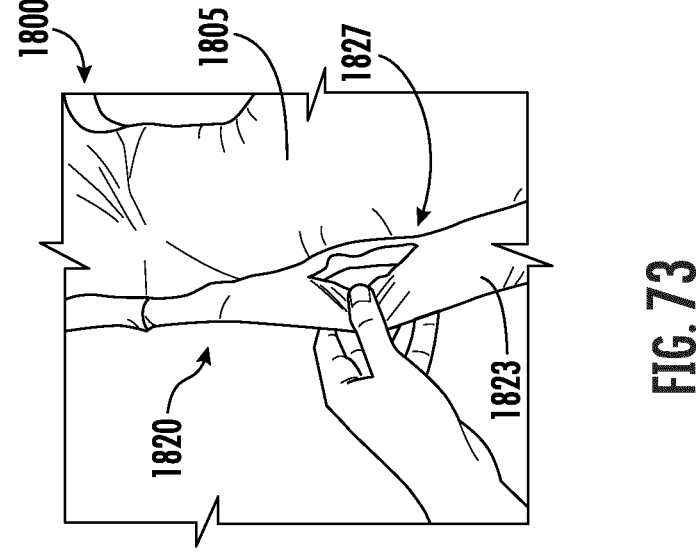
FIG. 73 shows a patient transfer device near an ergonomic handle, according to another exemplary embodiment.
Figure 72:
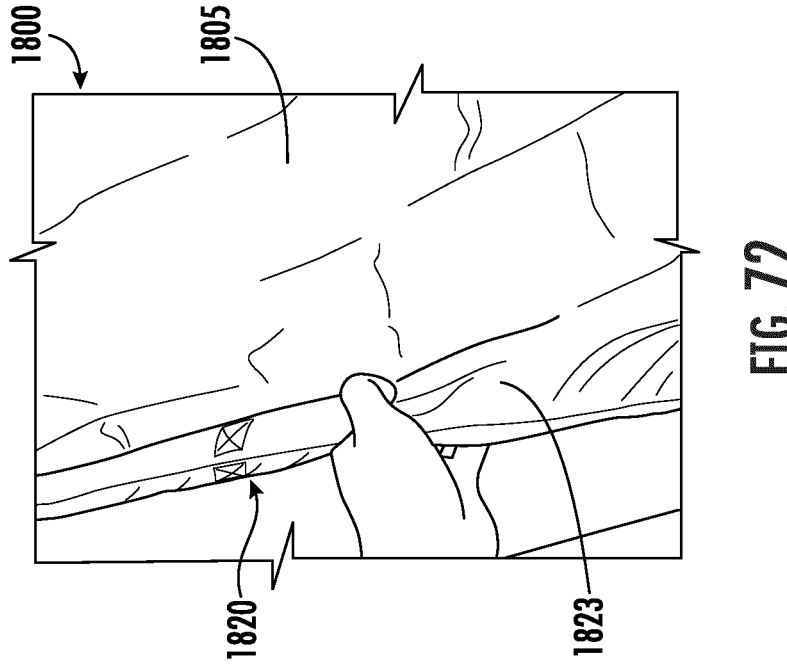
FIG. 72 shows a patient transfer device near an ergonomic handle, according to an exemplary embodiment.

In various embodiments, a patient transfer device may include one or more ergonomic features to facilitate handling of the device. FIGS. 72 and 73 show alternate views of an outer edge 1820 of a patient transfer device 1800 (similar or equivalent to any of the preceding patient transfer devices 100-1700), according to an exemplary embodiment. As shown, the patient transfer device 1800 includes a top surface 1805 configured to support a patient during transfer from a first surface to a second surface. The patient transfer device 1800 includes an outer edge 1820, which includes a cord 1823 sewn into a seam within the outer edge 1820 to facilitate grasping of the outer edge 1820 by a user. The outer edge 1820 may further include one or more apertures ("hand holes") 1827 disposed adjacent to the cord 1823. Accordingly, during use of the patient transfer device 1800, the user may insert a hand through an aperture 1827 and grasp onto the cord 1823 sewn into a seam within the outer edge 1820 to enable pulling of the patient transfer device 1800. The one or more apertures 1827 may be disposed through the entirety of the outer edge 1820 such that the user may grasp the cord 1823 using an overhand (i.e., palm facing downward) or an underhand (i.e., palm facing upward) grip.

In yet other embodiments, a patient transfer device may include handles formed by a fold within an outer edge of the patient transfer device. FIGS. 74-77 show alternate views of a patient transfer device 1900, according to an exemplary embodiment. The patient transfer device 1900 is configured for facilitating transfer of a patient from a first surface to a second surface. As shown, the patient transfer device 1900 includes an upper layer 1905 defining an upper surface and a lower layer 910 defining a lower surface. The upper layer 1905 and the lower layer 1910 are mutually joined along a shared outer perimeter. The upper layer 1905 and the lower layer 1910 form a chamber therebetween. The patient transfer device 1900 may also include a port (e.g., quick connect port), which may be configured for connection to one or more airflow devices to enable inflation and deflation of the patient transfer device 1900. In various embodiments, the one or more airflow devices may include, but are not limited to, air pumps, vacuums, compressors, etc.

Figures 74, 75, 76, 77:
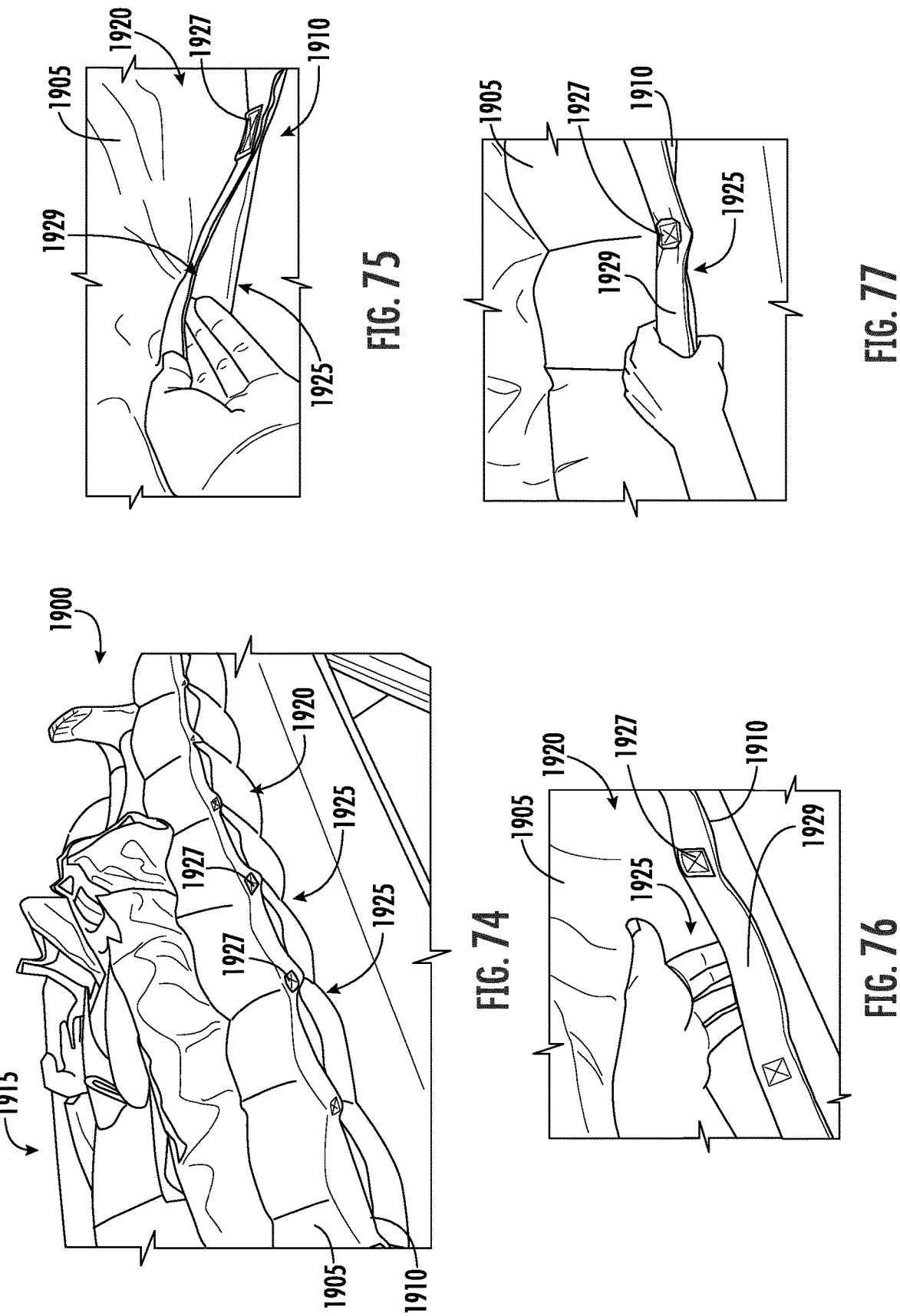
FIG. 74 shows a side perspective view of a patient transfer device having accordion handles, according to an exemplary embodiment.
FIGS. 75-77 show alternate views of an accordion handle of the patient transfer device of FIG. 74.

As shown, the patient transfer device 1900 includes a plurality of handles 1925 formed along an outer edge 1920 of the patient transfer device 1900. Each of the handles 1925 is formed by a dual fold 1929 within the outer edge 1920 and defined between sewn portions 1927. Accordingly, each of the handles 1925 may be grasped on a first side or a second side of the dual fold 1929 according to either an underhand (i.e., palm facing upward) or an overhand (i.e., palm facing downward) grip, as shown in FIGS. 75 and 76, respectively. In various embodiments, the patient transfer device 1900 may include the handles 1925 along an entire length of the outer edge 1920. In other embodiments, the handles 1925 may be disposed within a middle region of the outer edge 1920. In yet other embodiments, the handles 1925 may be disposed near an upper end and/or lower end of the patient transfer device 1900.

Figure 78:
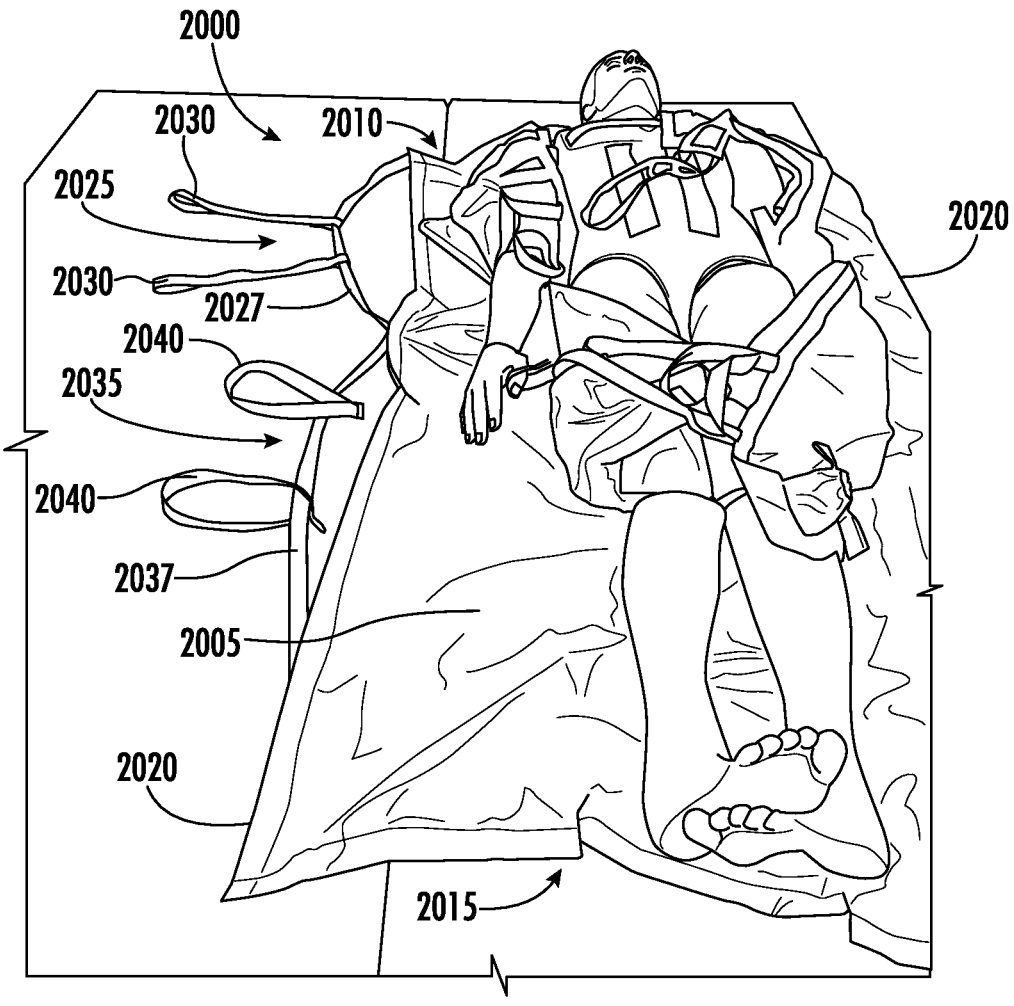
FIG. 78 shows a top perspective view of a patient transfer device having moveable straps, according to an exemplary embodiment.

In various embodiments, a patient transfer device may include one or more handle systems disposed along an outer edge of the device. FIG. 78 show alternate views of a patient transfer device 2000 (e.g., similar or equivalent to patient transfer devices 100, 200, 300, 400, 500, 600, 700, 800, 900, 1000, 1100, 1200, 1300, 1400, 1500, 1600, 1700, 1800, 1900), according to an exemplary embodiment. The patient transfer device 2000 includes an upper layer 2005 coupled to an opposing lower layer about a shared outer perimeter. In various embodiments, the upper layer 2005 and the lower layer are configured to form an inflatable chamber therebetween. Accordingly, the patient transfer device 2000 may also include one or more ports (e.g., quick connect ports), which are configured to facilitate connection to one or more devices to provide air for inflating the patient transfer device 2000. The patient transfer device 2000 includes a top edge 2010 and a bottom edge 2015. The patient transfer device 2000 further includes two substantially parallel outer edges 2020, which are disposed substantially perpendicular to each of the top edge 2010 and the bottom edge 2015. As shown, the patient transfer device 2000 includes a first handle system 2025 and a second handle system 2030, which are disposed along the outer edge 2020 and facilitate grasping, holding, pulling, or otherwise handling of the patient transfer device 2000.

As shown, the first handle system 2025 includes a longitudinal strap 2027, which connects to the edge 2020 of the patient transfer device 2000 at two terminal ends such that the strap 2027 extends in a direction that is substantially aligned with a longitudinal axis of the patient transfer device 2000. The strap 2027 is coupled to at least two extending handles 2030. Each of the handles 2030 includes a first end having a first loop, which surrounds the longitudinal strap, and a second end opposite the first end, wherein the second loop is configured to facilitate grasping or holding by a user (e.g., medical personnel). Each of the handles 2030 is configured such that the first loop is configured to facilitate movement of the handles 2030 relative to the strap 2027.

As shown, the second handle system 2035 includes a longitudinal strap 2037, which is similar or equivalent to the strap 2027. The strap 2037 is coupled to at least two extending handles 2040. Each of the handles 2040 form a singular loop, which surrounds the strap 2037. Accordingly, similar to the first handle system 2025, the loops of the handles 2040 facilitate movement of the handles 2040 relative to the strap 2037.

In each of the first handle system 2025 and the second handle system 2035, the handles 2030 and the handle 2040 may be configured to facilitate lifting of a patient positioned atop the patient transfer device 2000. In various embodiments, the handles 2030 and/or 2040 may be configured for attachment to one or more lifting devices or apparatuses (e.g., hoist), or the handles 2030 and/or 2040 may be configured for grasping by a user to facilitate manual lifting of a patient positioned atop the patient transfer device 2000. Respective movement of the handles 2030 and the 2040 relative to the straps 2027 and 2037 enable self-correcting positioning to facilitate centering of a lifting force (i.e., the lifting force needed to lift the patient). Accordingly, during use, each of the handles 2030 and/or 2040 may be coupled to one or more lifting mechanisms (e.g., hoist). During lifting, the handles 2030 and/or 2040 may subsequently displace relative to the strap 2027 and/or 2037, respectively, such that the lifting force is evenly distributed along the patient transfer device 2000.

Although FIG. 78 shows the patient transfer device 2000 having one of the first handle system 2025 and one of the second handle system 2035, various embodiments of the patient transfer device 2000 may exclusively include one or more of the first handle system 2025 or the patient transfer device 2000 may exclusively include one or more of the second handle system 2035. Although FIG. 78 shows handle systems 2025, 2035 disposed only on one outer edge 2020 of the patient transfer device 2000, various embodiments of the patient transfer device 2000 may include handle systems 2025, 2035 disposed on each opposing outer edge 2020.

In any of the preceding embodiments, one or more portions or components of the patient transfer device (e.g., patient transfer device 100, 200, 300, 400, 500, 600, 700, 800, 900, 1000, 1200, 1300, 1400, 1500, 1600, 1700, 1800, 1900, 2000) may consist of or comprise various polymers, natural, and/or synthetic materials. In various embodiments, one or more portions or components of the patient transfer device may consist of or comprise urethane. In various embodiments, various non-porous portions or components of the patient transfer device may comprise urethane coated nylon. In various embodiments, various porous components of the patient transfer device may comprise nylon. In various embodiments, various porous portions or components of the patient transfer device may have an air permeability ranging from approximately 5 cubic feet per minute (CFM) to approximately 20 CFM. In some embodiments, various portions or components of the patient transfer device may include a first side having a urethane coating and a second side having no coating, wherein the first side has a greater coefficient of friction compared to the second side.

Notwithstanding the embodiments described above in reference to FIGS. 1-78, various modifications and inclusions to those embodiments are contemplated and considered within the scope of the present disclosure.

As utilized herein with respect to numerical ranges, the terms "approximately," "about," "substantially," and similar terms generally mean +/−10% of the disclosed values, unless specified otherwise. As utilized herein with respect to structural features (e.g., to describe shape, size, orientation, direction, relative position, etc.), the terms "approximately," "about," "substantially," and similar terms are meant to cover minor variations in structure that may result from, for example, the manufacturing or assembly process and are intended to have a broad meaning in harmony with the common and accepted usage by those of ordinary skill in the art to which the subject matter of this disclosure pertains. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above.

It is important to note that any element disclosed in one embodiment may be incorporated or utilized with any other embodiment disclosed herein. For example, the upper and lower chambers 440, 445 of the exemplary embodiment described herein may be incorporated in the device 700 of the exemplary embodiment described herein. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. A patient transfer device comprising:
   a lower layer comprising:
      a top edge,
      a bottom edge, and
      a first side edge extending between the top edge and the bottom edge, the first side edge being perpendicular to at least one of the top edge or the bottom edge;
   an upper layer coupled to the lower layer at the top edge and the bottom edge, the upper layer comprising a second side edge parallel to the first side edge;
   a low-friction intermediate layer disposed between the upper layer and the lower layer the low-friction intermediate layer forming a loop about the lower layer such that the lower layer is disposed within the loop; and
   a handle disposed along at least one of the first side edge or the second side edge;
   wherein the low-friction intermediate layer is configured to slidably engage with the lower layer responsive to a pull force applied to the handle.

2. The patient transfer device of claim 1, further comprising a strap coupled to the first side edge, the strap extending outwardly from the first side edge towards a support surface,
   wherein the strap is configured to wrap around the support surface, thereby securing the patient transfer device to the support surface.

3. The patient transfer device of claim 1, wherein:
   the upper layer comprises a third side edge parallel to the second side edge; and
   the low-friction intermediate layer extends outwardly past the first side edge, the second side edge, and the third side edge in a direction parallel to the top edge and the bottom edge.

4. The patient transfer device of claim 1, wherein:
   the first side edge comprises a first top portion;
   the second side edge comprises a second top portion;
   the lower layer comprises a third top portion; and the first top portion, the second top portion, and the third top portion form three contiguous sides of a trapezoid.

5. The patient transfer device of claim 4, wherein the first side edge, the second side edge, and the bottom edge form three contiguous sides of a rectangle.

6. The patient transfer device of claim 1, wherein:
the bottom edge has a first length; and
the top edge has a second length, the second length being less than the first length.

7. The patient transfer device of claim 1, wherein:
the upper layer has a first height; and
the low-friction intermediate layer has a second height, the second height being less than the second height.

8. The patient transfer device of claim 1, wherein the low-friction intermediate layer is not coupled to the upper layer or the lower layer.

9. The patient transfer device of claim 1, wherein:
the upper layer comprises:
a top side, and
a bottom side;
at least a portion of the top side is coated with a coating;
the coating has a first coefficient of friction; and
the bottom side has a second coefficient of friction that is less than the first coefficient of friction.

10. The patient transfer device of claim 1, wherein the low-friction intermediate layer comprises a low-friction polymer material.

11. The patient transfer device of claim 1, wherein:
the lower layer comprises nylon; and
the upper layer comprises nylon.

12. The patient transfer device of claim 1, wherein:
the low-friction intermediate layer extends past the first side edge by a first length, and
the low-friction intermediate layer extends past the second side edge by a second length, the second length being equal to the first length.

13. The patient transfer device of claim 1, wherein the handle is formed as a cutout extending through at least one of the first side edge or the second side edge.

14. The patient transfer device of claim 1, wherein:
the upper layer is hexagonal; and
the lower layer is hexagonal.

15. The patient transfer device of claim 1, further comprising a strap coupled to the first side edge;
wherein the upper layer comprises a third side edge parallel to the second side edge; and
wherein the low-friction intermediate layer extends outwardly past the first side edge, the second side edge, and the third side edge in a direction parallel to the top edge and the bottom edge.

16. The patient transfer device of claim 15, wherein:
the first side edge comprises a first top portion;
the second side edge comprises a second top portion;
the lower layer comprises a third top portion; and
the first top portion, the second top portion, and the third top portion form three contiguous sides of a trapezoid.

17. The patient transfer device of claim 15, wherein:
the bottom edge has a first length; and
the top edge has a second length, the second length being less than the first length.

18. The patient transfer device of claim 15, wherein:
the upper layer has a first height; and
the low-friction intermediate layer has a second height, the second height being less than the second height.

19. The patient transfer device of claim 15, wherein the low-friction intermediate layer is not coupled to the upper layer or the lower layer.

20. The patient transfer device of claim 15, wherein:
the upper layer comprises:
a top side, and
a bottom side;
at least a portion of the top side is coated with a coating;
the coating has a first coefficient of friction; and
the bottom side has a second coefficient of friction that is less than the first coefficient of friction.

* * * * *